US012773176B2

(12) United States Patent
Mancardi et al.

(10) Patent No.: US 12,773,176 B2
(45) Date of Patent: Oct. 27, 2026

(54) METHODS AND APPARATUS TO SHARPEN A RADIOGRAPHIC IMAGE

(71) Applicant: GE Precision Healthcare LLC, Waukesha, WI (US)

(72) Inventors: Xavier Mancardi, Versailles (FR); Remy Andre Klausz, Neuilly sur Seine (FR)

(73) Assignee: GE Precision Healthcare LLC, Waukesha, WI (US)

(*) Notice: Subject to any disclaimer, the term of this patent is extended or adjusted under 35 U.S.C. 154(b) by 143 days.

(21) Appl. No.: 18/780,050

(22) Filed: Jul. 22, 2024

(65) Prior Publication Data

US 2026/0020834 A1 Jan. 22, 2026

(51) Int. Cl.

| | |
|---|---|
| ***A61B 6/00*** | (2006.01) |
| ***A61B 6/02*** | (2006.01) |
| ***G01T 1/20*** | (2006.01) |
| ***G06T 5/20*** | (2006.01) |
| ***G06T 5/73*** | (2024.01) |
| ***G06T 12/10*** | (2026.01) |

(52) U.S. Cl.

CPC ............ *A61B 6/5258* (2013.01); *A61B 6/025* (2013.01); *G01T 1/20181* (2020.05); *G06T 5/20* (2013.01); *G06T 5/73* (2024.01); *G06T 12/10* (2026.01); *G06T 2207/10112* (2013.01); *G06T 2207/10116* (2013.01); *G06T 2210/41* (2013.01)

(58) Field of Classification Search

CPC ........ A61B 6/5258; G01T 1/2018; G06T 5/73

See application file for complete search history.

(56) References Cited

U.S. PATENT DOCUMENTS

| | | | | |
|---|---|---|---|---|
| 9,916,656 | B2 | 3/2018 | Choi et al. | |
| 12,198,300 | B2 * | 1/2025 | Yang | G06N 3/094 |
| 2010/0053203 | A1 | 3/2010 | Bernhardt et al. | |
| 2012/0114212 | A1 * | 5/2012 | King | G06T 12/20<br>382/131 |
| 2016/0019678 | A1 * | 1/2016 | Cecil | G16H 50/20<br>378/62 |
| 2023/0007835 | A1 * | 1/2023 | Ratcliffe | G06T 5/50 |
| 2023/0306657 | A1 | 9/2023 | Sehnert | |

FOREIGN PATENT DOCUMENTS

| | | |
|---|---|---|
| EP | 3662839 B1 | 7/2023 |

OTHER PUBLICATIONS

Cha et al., "Development of Adaptive Point-Spread Function Estimation Method in Various Scintillation Detector Thickness for X-ray Imaging," MDPI, Sensors 2023, published Sep. 30, 2023, 20 pages.

(Continued)

*Primary Examiner* — Hugh Maupin

(57) ABSTRACT

Systems, apparatus, articles of manufacture, and methods are disclosed to sharpen a radiographic image by capturing a radiographic image with a detector receiving a beam from a source and performing a digital correction to the radiographic image to generate a digital image with increased uniformity in sharpness compared to the radiographic image.

17 Claims, 20 Drawing Sheets

(56) References Cited

OTHER PUBLICATIONS

Dakovic et al., “Mammograms Restoration by Restoration by Using Wiener Filter,” American Institute of Physics Conference Proceedings, URL:[http://dx.doi.org/10.1063/1.4944309], Mar. 25, 2016, 4 pages.
Kim et al., “Fourier Analysis of Multi-Scale Neural Networks Implemented for High-Resolution X-Ray Radiography,” NDT&E International 139, Elsevier, Jul. 27, 2023, 9 pages.
Romualdo et al., “Mammographic Image Denoising and Enhancement Using the Anscombe Transformation, Adaptive Wiener Filtering, and the Modulation Transfer Function,” J Digit Imaging, Society for Imaging Informatics in Medicine, Jul. 18, 2012, 15 pages.
Urbanczyk et al., “Characterization of the Effects of the FineView Algorithm for Full Field Digital Mammography,” IOP Publishing, Physics in Medicine and Biology, Mar. 20, 2012, 19 pages.
Zhang et al., “MTF Compensation for Digital Radiography System With Indirect Conversion Flat Panel Detector,” GE Healthcare, Mammography Engineering, downloaded Jun. 26, 2016, 8 pages.
EP application 25187638.9 filed Jul. 4, 2025—extended Search Report issued Nov. 27, 2025; 11 pages.
Rührnschopf and Ernst-Peter et al: “A general framework and review of scatter correction methods in cone beam CT. Part 2: Scatter estimation approaches”, Medical Physics, AIP, Melville, NY, US, vol. 38, No. 9, Sep. 1, 2011 (Sep. 1, 2011), pp. 5186-5199, XP012151167, ISSN: 0094-2405, DOI: 10.1118/1.3589140 [retrieved on Aug. 25, 2011] * section IV.C *.

* cited by examiner

METHODS AND APPARATUS TO SHARPEN A RADIOGRAPHIC IMAGE

FIELD OF THE DISCLOSURE

This disclosure relates generally to image processing and, more particularly, to sharpening a radiographic image.

BACKGROUND

X-ray imaging systems are valuable tools in medical applications such as to assist in diagnosis and treatment of a variety of diseases and/or other medical conditions. Some X-ray imaging systems include a detector that converts received X-rays into a signal. In a specific variety of detectors, in an intermediate stage, the X-ray photons are first converted into light. The light (e.g., photons) forms an image representative of received light intensity levels that can be further processed and analyzed. Deficiencies in the image can impact the usefulness of that image for processing and analysis.

Figure 1:
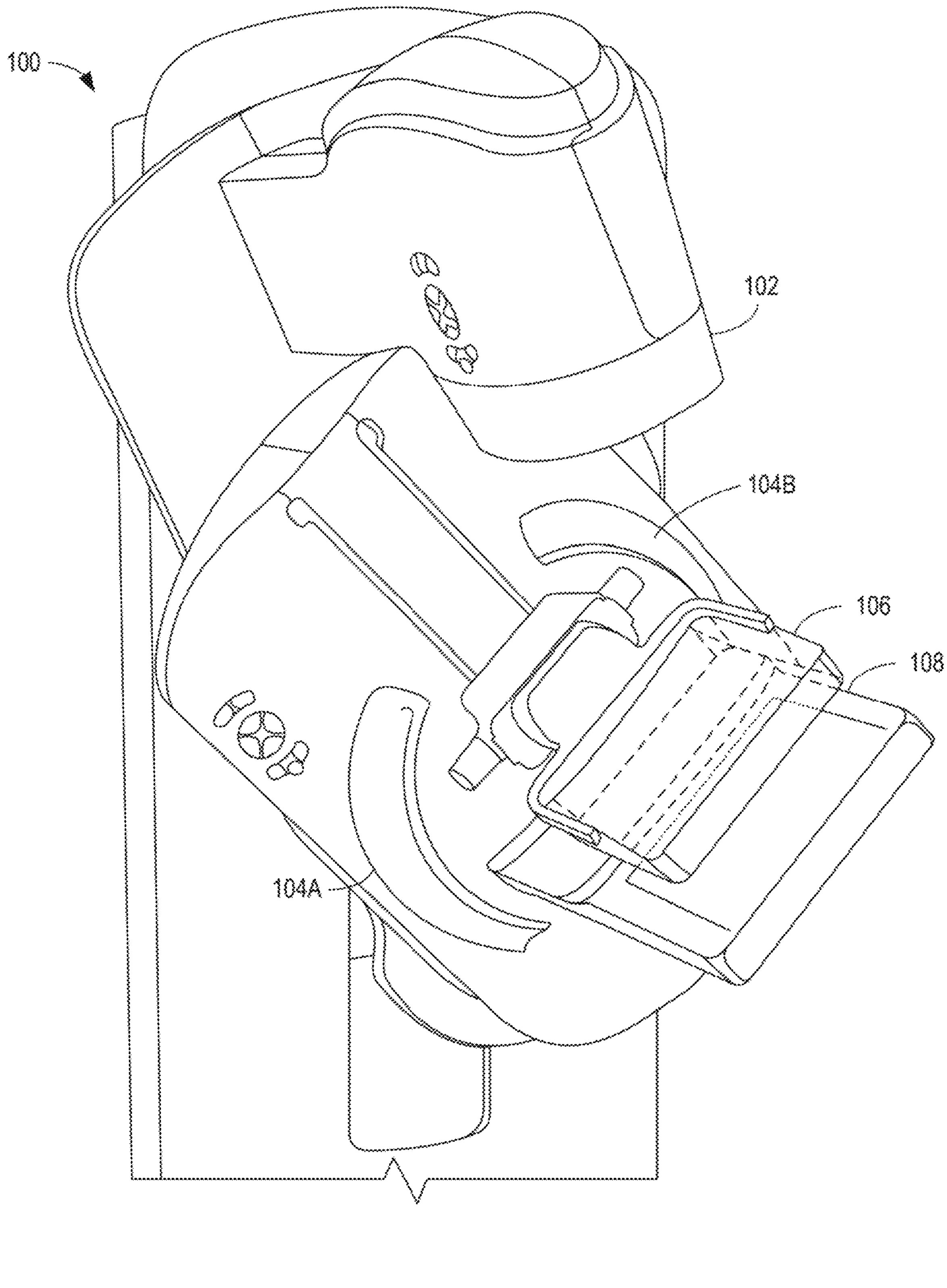
FIG. 1 illustrates a medical imaging device that is shown in a rotated position.

In general, the same reference numbers will be used throughout the drawing(s) and accompanying written description to refer to the same or like parts. The figures are not necessarily to scale. Instead, the thickness of the layers or regions may be enlarged in the drawings. Although the figures show layers and regions with clean lines and boundaries, some or all of these lines and/or boundaries may be idealized. In reality, the boundaries and/or lines may be unobservable, blended, and/or irregular.

DETAILED DESCRIPTION

Medical imaging devices capture two-dimensional (2D) images and/or three-dimensional (3D) images using a plurality of methods including ultrasound, X-ray, gamma ray, computed tomography (CT) scan, tomosynthesis, magnetic resonance imaging (MRI), etc. Some medical imaging devices are used in mammography to detect cancer in anatomy such as a patient breast. In mammography, the images are to have a high resolution and wide dynamic range. The mammographic images are to have a high sensitivity to detect and depict small structures (e.g., micro-calcifications, fibers, etc.).

Medical images, such as radiographic images created using X-rays, are not perfect representations of an object (e.g., breast(s), etc.) being imaged. Rather, captured radiographic images depict interactions between X-rays and an object (e.g., patient breast(s)). For example, X-ray images are projections of the interactions of three-dimensional objects with the X-rays on a plane. The X-ray images are not perfectly clear due to imperfections of the medical imaging device (e.g., imperfect detector, imperfect source, etc.). Imperfections in the medical imaging device and/or an environment in which the breast is imaged introduce blurriness and/or other artifact in resulting radiographic images, which hinders a radiologist or a machine with computer-aided detection from proper processing and analysis of the images (e.g., to determine whether a patient is likely to have cancer).

If a radiologist or a machine with computer-aided detection is unable to properly diagnose and/or determine next step(s) for a patient, subsequent images may be unnecessarily requested, which wastes processor cycles, patient, staff time, and other healthcare resources. In addition to wasting healthcare resources, these subsequent radiographic images involve an additional radiation dose to the patient, which may have adverse health effects due to repeated exposure to radiation.

In some examples, the radiologist may use an image processing technique to increase image quality (e.g., image sharpness, image clarity, image contrast, image resolution, etc.) of the captured radiographic images. There are various techniques to increase image sharpness. One of these techniques is to apply a uniform convolution kernel to the initial radiographic image as a correction term over the entire image (corresponding to an entire medical imaging device detector). However, this technique does not account for variation in a detector, including different angles at which an imaging beam contacts different areas of the detector. Techniques disclosed herein determine and apply localized digital correction such as local convolution kernels and/or other local spatial filtering to compensate for detector effects. For example, local convolution kernels can be selected from a set of convolution kernels to different portions of the initial radiographic image corresponding to different areas of the detector. Techniques disclosed herein use the plurality of localized convolution kernels to generate a more accurate radiographic image that is sharper (e.g., has a sharpness that is more uniform across the detector) when compared to radiographic images generated with the uniform, single-kernel technique. Techniques disclosed herein include calculating local convolution kernels to apply different corrections to different areas of an obtained image to generate a more accurate radiographic image. The techniques disclosed herein include performing a digital correction (e.g., a digital computation, localized digital correction, etc.) on the initial radiographic image by filtering in Fourier space, artificial intelligence methods, and using a non-stationary, variable convolution kernel function. In some examples, the variable convolution kernel function is characterized as a continuous kernel or a continuous kernel function (e.g., defined as a function of detector location and/or beam angle). In some examples, the non-stationary, continuous, variable convolution kernel function is to, for various inputs, generate kernel coefficients as outputs.

Turning to the figures, FIG. 1 illustrates an example medical imaging device 100 that is shown in a rotated position. The example medical imaging device 100 includes an example source 102, an example left arm bar 104A, an example right arm bar 104B, an example support tray 106, and an example detector 108. In mammography imaging, the patient places a left hand on the curved surface of the left arm bar 104A, a right hand on the curved surface of the right arm bar 104B, and breasts on the support tray 106. While this example is described in the context of mammography, the machine and associated processes described herein can be applied to radiographic imaging of other objects. The source 102 (e.g., beam emitter) includes an aperture that emits a beam (e.g., X-ray, etc.) which interacts with the detector 108 (e.g., detector plate, detection surface, etc.). In the example of FIG. 1, the detector 108 is a flat-panel detector that is located behind the object to be imaged (e.g., the breasts of the patient) which is located underneath the source 102. The beams from the source 102 interact with the inner structures of the object to be imaged, and the inner structures are represented by the relative intensity of the signals captured. Different tissues of the human body have different features which may involve different radiation dose, resulting in varying levels of signal strength and noise in the received image data.

Figure 2:
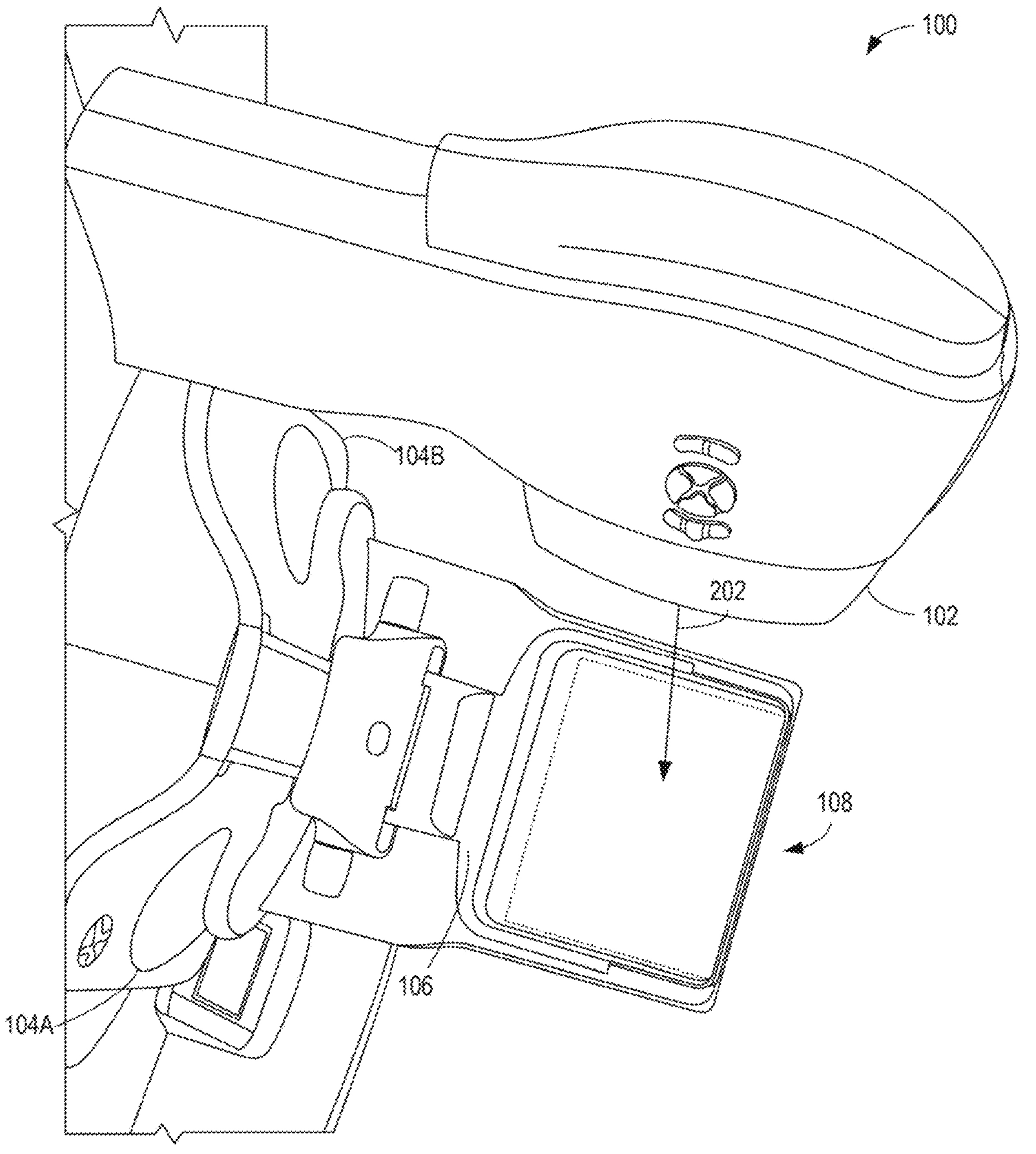
FIG. 2 illustrates the detector of the medical imaging device and the support platform of the medical imaging device.

As shown in the example of FIG. 2, once the medical imaging device 100 is initialized, the source 102 of the medical imaging device 100 emits a beam 202 (e.g., radiation, wave, signal). The beam 202 passes through the breast and its internal structures, as well as the support tray 106, before impacting the detector 108.

In some versions of mammography (e.g., digital breast tomosynthesis (DBT)), multiple images are taken at different positions (e.g., different gantry angles) as the source 102 of medical imaging device 100 is rotated with respect to the breast being imaged, as shown in the example of FIG. 1. The multiple images can then be stitched together by the medical imaging device 100 to generate a three-dimensional (3D) rendering of the breast of the patient (e.g., a three-dimensional digital breast tomosynthesis image).

The techniques disclosed herein may use a direct conversion detector (e.g., typically manufactured with amorphous selenium (a-Se), thallium bromide, and gadolinium compounds) or an indirect conversion detector (e.g., typically manufactured with thallium-doped cesium iodide (CsI:Tl), gadolinium oxysulfide, terbium-doped gadolinium oxysulfide ($Gd_2O_2S$:Tb), barium fluoride, or cadmium tungstate ($CdWO_4$), for example. In some examples, the direct conversion detectors use a first layer to receive X-ray photons and convert the X-ray photons into electric charges. The electric charges are then converted into a digital signal. In some examples, the indirect conversion detectors first convert the X-rays into light. The light is then converted into an electrical signal. The electrical signal is then converted into a digital signal. In some examples, the medical imaging device 100 (e.g., the Senographe Pristina™ manufactured and sold by GE HealthCare) is an indirect conversion detector full-field digital mammography system with a cesium iodide (CsI) crystalline phosphor coupled to an amorphous silicon thin-film transistor array. The photons of the beam 202 impact the detector 108 as discussed in connection with FIG. 3.

Figure 3:
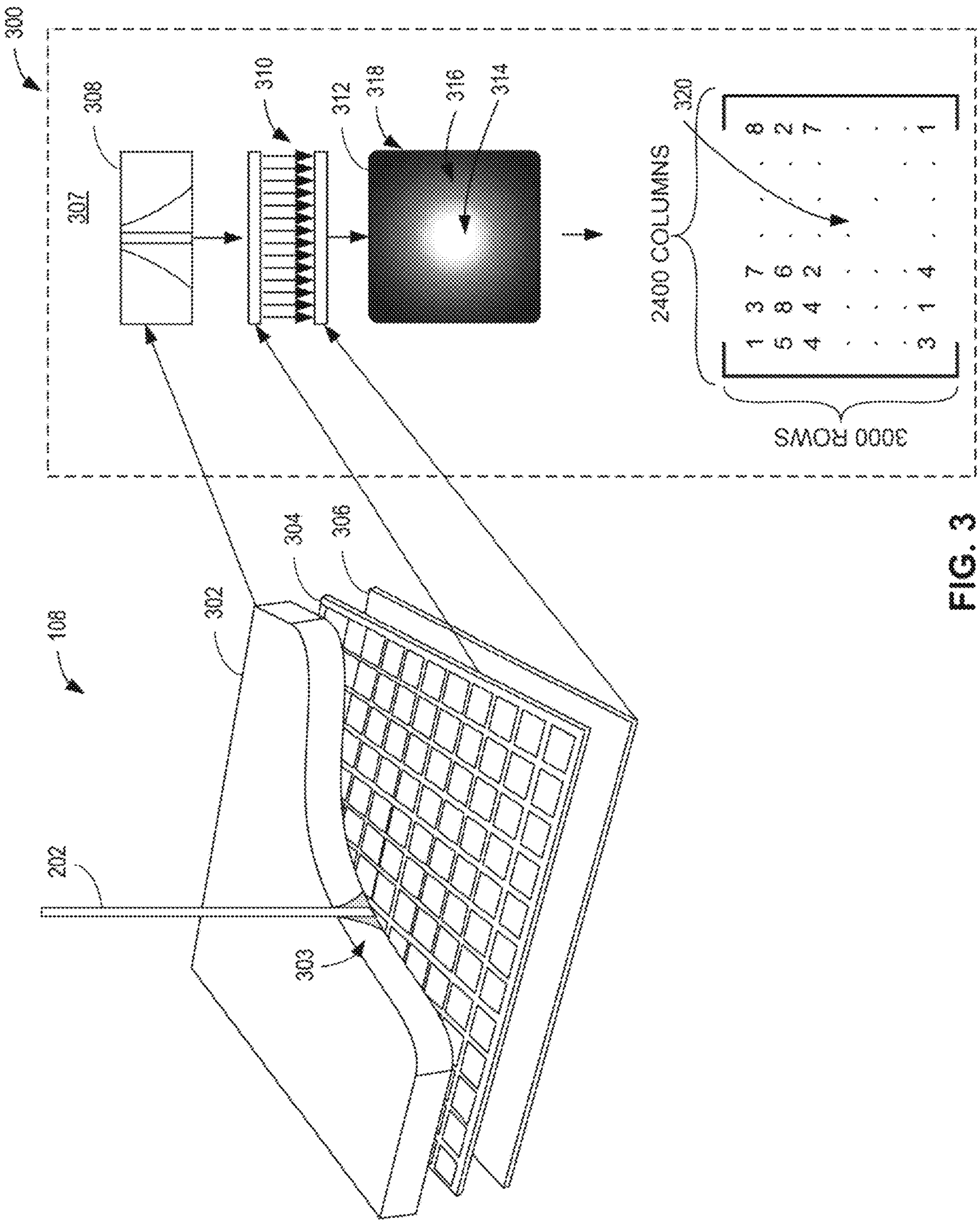
FIG. 3 illustrates internal components of the detector of the medical imaging device.

FIG. 3 illustrates an example scintillation process 300. The scintillation process 300 describes at least one method to generate a radiographic image based on an impingement of the beam 202 on the detector 108. In the example of FIG. 3, the beam 202 is an X-ray beam. The beam 202 is shown interacting with an example scintillator layer 302 (e.g., first layer, top layer, layer of scintillation material, etc.) of the detector 108. A portion of the beam 202 is referred to as beam spread 303, which spreads outward through the scintillator layer 302. The beam 202 spreads to a photodiode layer 304 (e.g., second layer, middle layer, layer of photodiodes, etc.) of the detector 108. Individual photodiodes are represented as squares of the photodiode layer 304 in the example of FIG. 3. The photodiodes of the photodiode layer 304 separate the beam 202 into electric signals as the beam 202 passes into an electronic layer 306 (e.g., a third layer, a bottom layer, a circuitry layer, etc.) of the detector 108.

As shown in callout 307, the beam spread 308 is shown as being separated by the photodiodes 310 which produce the initial image 312. The center of the beam (e.g., a contact point) is shown as a first region 314 (e.g., a white region) with some of the spread shown as a second region 316 (e.g., a light gray region) that surrounds the first region 314 and portions that were not impacted are shown as a third region 318 (e.g., black region). Scintillation generates electrical signals in adjacent locations to a contact point of the energy of an X-ray beam (e.g., the beam 202 of FIG. 2) that contacts a generally flat detector (e.g., the detector 108 of FIG. 2). The contact of the photons of the X-ray beam 202 generates electrical signals in the contacted photodiodes 310 of the first region 314, adjacent photodiodes 310 of the second region 316, and some photodiodes 310 of the third region 318 that are further away. These photodiodes 310 produce signals that are representative of light intensity values. The electronic layer 306 then converts the signals, which are representative of light intensity values, into pixels in the initial image 312 where a reduction in contrast (e.g., a decrease in sharpness) of the pixels corresponds with electrical signals that are farther away from the contact point.

As shown in the initial image 312, blurring (e.g., point-spread) and/other artifact can occur in at least some of the pixels based on a quality of the signals generated. The medical imaging device 100 applies one or more imaging processing algorithms to sharpen (e.g., un-blur) the initial image 312 as described further below. The medical imaging device 100, to apply the one or more imaging processing algorithm, converts the initial image 312 into an initial image pixel matrix 320. The one or more imaging processing algorithms perform operations on the individual pixel values that compose the initial image pixel matrix 320. These one or more imaging processing algorithms change the values of the initial image pixel matrix 320 to generate a corrected image pixel matrix which is then converted back into a visual format as a corrected image that radiologist or a machine with computer-aided detection can evaluate. The one or more imaging processing algorithms that are implemented by the example medical imaging device 100 are further discussed below, before returning to an example discussion of how the medical imaging device 100 operates in FIG. 4. The one or more imaging processing algorithms correct the initial image 312 due to characteristics of the detector 108.

Quality of a resulting image can be dependent on characteristics of the detector 108 to translate the received beam 202 into signals representative of light intensity and/or other information. A modulation transfer function (MTF) quantifies an ability of the detector 108 to accurately convert the received beam 202 into electrical signals that convey information about an object, including contrast in and around the object to form a resulting image. For example, MTF quantifies how well the medical imaging device 100 transfers contrast of sinusoidal patterns from the incident X-ray pattern to the output. In other words, MTF measures how the medical imaging device 100 transmits signal, as a function of special frequency. The MTF can be expressed in terms of spatial frequency and signal amplitude. For example, the detector 108 has a certain limited spatial resolution. This limited spatial resolution causes a loss in contrast in the initial image 312. A perfect MTF is equal to 1 at all frequencies.

For example, the spatial resolution of the detector 108 relates to an ability of the scintillator layer 302 to receive and translate the beam 202. For example, the scintillator layer 302 transforms the incoming X-ray beam 202 into a plurality of optical photons, which scatter in the scintillator (e.g., a Cesium Iodide (CsI) scintillator, etc.). The scattering of photons in the scintillator layer 302 transforms a single point into a wider area (e.g., a point spread function), which affects the MTF. The change (e.g., decrease) in the MTF is indicative of a loss in resolution (and associated image contrast) from a point to a spread of values in the detector 108.

The MTF of the detector 108 relates contrast values of the object(s) being imaged into contrast intensity levels in the initial image 312. The MTF of the detector 108 can be used on a measure of image resolution because the function accounts for blur and contrast over a range of spatial frequencies. The MTF represents an ability of the detector 108 to transfer modulation of an input signal to an output at a given spatial frequency. However, the MTF for the detector 108 can be degraded or otherwise affected.

Loss of contrast or other image degradation caused by the detector 108 MTF can be accounted for through convolution or filtering. However, conventional convolution assumes that the MTF remains constant over all areas of the detector 108 using a single, uniform convolution kernel (as discussed in FIG. 4A). The kernel is a mask or matrix used in convolution to adjust pixel values. For example, the convolution kernel is a matrix or grid that aligns with the number of pixels in the initial image 312. A convolution between the convolution kernel and the initial image 312 produces a processed image in which contrast between small details and high spatial frequencies is heightened and blurriness is removed resulting in improved sharpness or clarity. However, assuming a single, uniform convolution kernel for all portions of the detector 108 leads to imperfect/inaccurate convolution such that blurriness and/or other artifact(s) remain in the resulting image.

More specifically, the initial image 312 (e.g., a detector image, etc.) is convolved with a sharpening term (e.g., a correction term):

$$I * K = C. \quad \text{(Equation 1)}$$

In Equation 1, an initial image I is convolved (represented by the asterisk "*") with a convolution kernel K (e.g., a correction term) to generate a corrected image C. In some examples, before convolving the initial image I with the convolution kernel K, the medical imaging device 100 performs pre-processing on the initial image 312. This pre-processing includes applying a gain filter (e.g., gain correction), applying an offset filter (e.g., offset correction), and/or removing bad pixels (e.g., correcting for detector elements). As used herein, removing bad pixels includes removing pixels that are malfunctioning by always transmitting white light (e.g., always turned on), always transmitting black (e.g., always turned off), or other defect. In some examples, the pre-processing optionally includes applying a noise filter (e.g., noise correction).

The techniques disclosed herein use an adaptive convolution kernel in lieu of a single convolution kernel K. As used herein, the adaptive convolution kernel may refer to either a set of discrete local convolution kernels (e.g., a library of discrete local convolution kernels) or an adaptive local convolution kernel function. As such, a localized convolution kernel can be generated by selecting one of the set of local convolution kernels or by executing the adaptive convolution kernel function according to local parameters such as angle between source and detector, position/location on the detector, etc. In some examples, the local convolution kernels $K_{x,y}$ are based on local detector information. One example of the local detector information corresponds to a position or location (e.g., x-coordinate, y-coordinate) on the surface of the detector 108 (FIG. 1). Another example of the local detector information corresponds to angles of the detector 108 (FIG. 1) and the source 102 (FIG. 1). That is, a library or set of local convolution kernels $K_{x,y}$ includes kernels for various areas (e.g., regions, positions, locations, etc.) of the detector 108 and can also include convolution kernel variations for those positions at different angles between the source 102 and the detector 108. Equation 2 substitutes the uniform convolution kernel K with the local convolution kernels $K_{x,y}$:

$$I * K_{x,y} = C. \quad \text{(Equation 2)}$$

In Equation 2, the initial image I is convolved (represented by the asterisk "*") with the local convolution kernels $K_{x,y}$ (e.g., local correction terms) to generate a corrected image C. The techniques of Equation 2 are implemented by the medical imaging device 100 as shown in connection with FIG. 4B.

In some examples, the techniques of Equation 2 are implemented by the medical imaging device 100 in connection with a Wiener filter used in a sharpening algorithm (e.g., the GE HealthCare Fine View™ sharpening algorithm, etc.). The Wiener filter is to modify an amount of correction applied by the kernel K based on an amount of noise. The Wiener filter substitutes the correction term that is convolved with the initial image I to generate the corrected image C:

$$I\left[\frac{H}{|H|^2 + W}\right] = C. \quad \text{(Equation 3)}$$

In Equation 3, H is the Fourier transform of the point-spread function of the scintillator layer 302 (FIG. 3). In some examples, values for the Fourier transform of the point spread function of the scintillator layer H are between 0 and 1. W is the Wiener spectrum value at the same frequency as H. In some examples, values for the Wiener spectrum value W that is at the same frequency as the Fourier transform of the point spread function of the scintillator layer are between 0 and 5. In some examples, W is defined as power-spectral density of noise n divided by power-spectral density of object s (e.g., noise power spectrum divided by signal spectrum) as shown below in Equation 3:

$$W = \left|\frac{n}{s}\right|^2. \quad \text{(Equation 4)}$$

The W term of the Wiener filter acts as a modifier to regulate correction of the MTF in the presence of noise. For example, if there is no noise (e.g., zero in the numerator of Equation 4), the Wiener filter barely reduces the amount of correction that is applied to adjust signal values. In some examples, values for the power-spectral density of noise n are between 0 and 0.5. In some examples, values for the power-spectral density of object s are between 0 and 5. In some examples, a higher value of W may be around 0.3 which would warrant less correction compared to a lower value of W of around 0.03 which would warrant higher amounts of correction.

For example, using numbers merely for illustration, H is a constant value such as 0.5. A Wiener filter with H as 0.5 without any noise is shown in Equation 5:

$$I\left[\frac{0.5}{|0.5|^2 + 0}\right] = C. \quad \text{(Equation 5)}$$

Equation 5 is simplified to generate Equation 6:

$$I * 2.0 = C. \quad \text{(Equation 6)}$$

In the example of Equation 6, the amount of correction is a value of 2.0. This value will be reduced by either a large amount (e.g., a significant amount of reduction, a large amount of reduction) or reduced by a small amount (e.g., a mild amount of reduction, a lesser amount of reduction). The amount of reduction of the amount of correction is based on the Wiener spectrum value W which is based on an amount of noise.

For example, if there is a higher amount of noise (e.g., a large number in the numerator of Equation 4), the Wiener filter significantly reduces an amount of correction. The higher amount of noise corresponds to a large Wiener spectrum value W (e.g., 0.3) in Equation 4. The large Wiener spectrum value W of Equation 4 is in the denominator of Equation 3 which reduces the amount of correction. Equation 7 illustrates an example that also assumes that H is a value such as 0.5:

$$I\left[\frac{0.5}{|0.5|^2 + |0.3|^2}\right] = C. \quad \text{(Equation 7)}$$

Simplifying the terms of Equation 7, results in Equation 8:

$$I\left[\frac{0.5}{0.25 + 0.09}\right] = C. \quad \text{(Equation 8)}$$

Simplifying the terms of Equation 8 results in Equation 9:

$$I * 1.470588 = C. \quad \text{(Equation 9)}$$

As seen in Equation 9, there is a significant reduction in the amount of correction used with the initial image I to generate the corrected image C. The initial amount of correction was 2.0, while the correction has been reduced to 1.47.

Alternatively, if there is a lesser amount of noise (e.g., a small number in the numerator of Equation 4), the Wiener filter reduces an amount of correction at a reduction level that is not as extreme as the Wiener filter of Equations 7-9. The lesser amount of noise corresponds to a small Wiener spectrum value W (e.g., 0.03) in Equation 4. The small Wiener spectrum value W of Equation 4 is in the denominator of Equation 3 which reduces the amount of correction.

Equation 10 illustrates an example that also assumes that H is a value such as 0.5:

$$I\left[\frac{0.5}{|0.5|^2+|0.03|^2}\right]=C. \quad \text{(Equation 10)}$$

Simplifying the terms of Equation 10, results in Equation 11:

$$I\left[\frac{25}{0.25+0.0009}\right]=C. \quad \text{(Equation 11)}$$

Simplifying the terms of Equation 11 results in Equation 12:

$$I*1.992826=C. \quad \text{(Equation 12)}$$

As shown in Equation 12, the amount of correction is 1.99 reduced from an initial correction of 2.0. As shown in Equations 6-12, when there is less noise, there is more of a correction and when there is more noise, there is less of a correction. Stated differently, Wiener filtering (e.g., minimum mean-square-error filtering) approximates inverse filtering when there is little noise (e.g., "low" noise, such as when W is 0.03), and approximates a frequency-rejection filter when there is a significant amount of noise (e.g., "high" noise such as when Wis 0.3). For example, there may be little noise if the source 102 is directly over the detector 108, and lots of noise if the source 102 is not aligned over the detector 108.

An inverse Fourier Transform is applied to the Wiener filter to change Equation 3 from Fourier space to real space. The inverse Fourier Transform generates a convolution kernel which is an array (e.g., or matrix) of values. In some examples, the inverse Fourier Transform is an inverse Fast Fourier Transform.

The techniques of Equation 2 are implemented by the medical imaging device 100 in connection with an adapted Wiener filter (e.g., a local Wiener filter) used in a sharpening algorithm (e.g., the GE HealthCare Fine View™ sharpening algorithm, etc.). Equation 13 illustrates an adapted Wiener filter where H is based on various positions x and y of the detector 108 (FIG. 1):

$$I\left[\frac{H_{x,y}}{|H_{x,y}|^2+W}\right]=C. \quad \text{(Equation 13)}$$

After calculating Equation 13, the medical imaging device 100 uses an inverse Fourier Transform to generate a set of noise-adjusted local kernels that are based on the position of the detector 108 (FIG. 1).

Equation 14 illustrates an adapted Wiener filter where His based on various angles between the detector 108 (FIG. 1) and the source 102 (FIG. 1):

$$I\left[\frac{H_{\theta}}{|H_{\theta}|^2+W}\right]=C. \quad \text{(Equation 14)}$$

After calculating Equation 14, the medical imaging device 100 uses an inverse Fourier Transform to generate a set of noise-adjusted local convolution kernels that are based on the angle between the detector 108 (FIG. 1) and the source 102 (FIG. 1). In other examples, the medical imaging device 100 uses radiation dose (FIG. 12) to determine H, or a combination of position, angle, and dose to determine H.

Equations 13 and 14 are based on the adaptive local convolution kernel function. By interpolating between different variables, the adaptive local convolution kernel function dynamically generates more accurate local convolution kernels based on the parameters of the adaptive local convolution kernel function. For example, a discrete local convolution kernel can be generated for a particular detector location based on an angle between the detector 108 and the source 102.

The medical imaging device 100 and/or a computing device associated with the medical imaging device 100 can apply a localized digital correction (e.g., local spatial filtering such as with an adaptive convolution kernel, model, etc.) to generate images with increased contrast between small details and high spatial frequencies, resulting in improved sharpness or clarity. For example, a MTF (local or overall) can be determined outside the medical imaging device 100 based on an image acquired by the medical imaging device 100 of a known reference object, or by computation using a model of the detector 108, etc. In some examples, MTF is defined as a ratio of output signal amplitude to input signal amplitude (e.g., corresponding to an amount of contrast that is preserved by the detector 108). A higher MTF score corresponds to a sharper image (e.g., an MTF of 1.0 corresponds to 100% of an input signal amplitude being transmitted by the detector 108; an MTF of 0.5 indicates a 50% signal degradation).

In typical methods, the convolution kernel K is determined based on a standard set of values for the entire detector 108. A further discussion of how the local convolution kernels $K_{x,y}$ is determined is included in connection with FIG. 4B. In typical methods, the medical imaging device 100 determines the convolution kernel K once which is then applied to all datapoints of the initial image 312 (FIG. 3). However, by applying a universal convolution kernel (e.g., a homogenous convolution kernel, a uniform convolution kernel) over the entire detector 108, only certain areas of the image are improved. However, in typical methods, the universal convolution kernel is determined based on one fixed position between the source 102 and the detector 108. This one measurement does not take into account that the detector 108 is not uniform. In addition, this one measurement does not account for movement of the source 102, which changes the relative position between the source 102 and the detector 108 to obtain a plurality of images taken in various positions as the source 102 of the medical imaging device 100 moves (e.g., rotates or revolves) around the object being imaged with respect to the detector 108. During the revolution of the source 102 around the stationary object (e.g., a patient anatomy), the medical imaging device 100 captures multiple images. These images are combined to generate a 3D image.

Rather than maintain a uniform or fixed convolution kernel to be applied to the entire detector 108, the techniques disclosed herein perform a digital correction (e.g., a local digital correction, local spatial filtering, etc.). One example method of performing the digital correction is to use an adaptive convolution kernel (e.g., a discrete library of values or a non-stationary function that generates output values based on inputs, etc.). In some examples, the techniques disclosed herein use an adaptive convolution kernel function that is continuous.

In some examples, the adaptive convolution kernel is formed as a matrix of N×P coefficients. The coefficients are a function of parameters such as a position (x,y) in the detector 108, an angle (θ,ϕ) of a ray from the X-ray source 102 to a specific point of the detector 108, or position (x,y) and current tomographic angle of the source 102 (e.g., an X-ray tube, etc.) relative to a plane normal to the detector plane, or a combination thereof.

In some examples, the techniques disclosed herein use an adaptive convolution kernel by determining multiple local convolution kernels (e.g., a non-uniform set of convolution kernels corresponding to a plurality of source/detector positions). This plurality of adaptive convolution kernels is applied to respective images corresponding to particular locations to further deconvolve the image. The medical imaging device 100 is to adaptively determine which convolution kernel of the non-uniform set of local convolution kernels to apply for specific portions of the image (as described in connection with FIG. 4B).

Figure 4A:
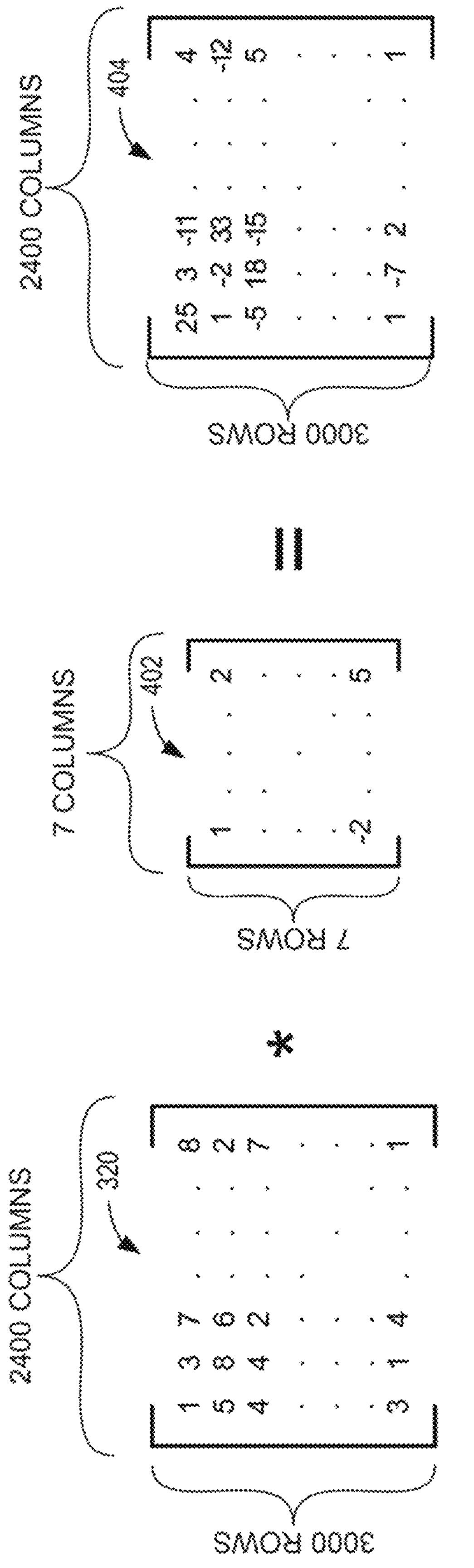
FIG. 4A illustrates a technique that uses a uniform convolution kernel to sharpen an initial radiographic image captured by the medical imaging device to generate a uniformly sharpened image.

FIG. 4A illustrates a technique that uses a uniform convolution kernel 402 to sharpen the initial image pixel matrix 320 that corresponds to the initial image 312 (FIG. 3) (e.g., radiographic image) captured by the medical imaging device 100 (FIG. 1). The initial image pixel matrix 320, in the example of FIG. 4, is represented as a matrix of two thousand and four hundred (2,400) columns and three thousand rows (3,000) based on a detector 108 (FIG. 1) with a length of twenty-four 24 centimeters and a width of thirty 30 centimeters. However, in other examples, the number of columns and rows can correspond to other values such one thousand (1,000), six thousand (6,000), or ten thousand (10,000).

The initial image pixel matrix 320 is represented in FIG. 4A as a 2,400 by 3,000 matrix (e.g., 2,400×3,000 matrix) with partially filled in data. The uniform convolution kernel 402 is represented as a matrix of seven rows and seven columns (e.g., a 7 by 7 (7×7) matrix) with partially filled in data. However, in other examples, the uniform convolution kernel 402 has different dimensions (e.g., a 9×9 matrix, a 3×3 matrix, etc.). The uniform convolution kernel 402 has odd dimensions which results in a central point in performing the convolutions.

The example medical imaging device 100 performs image convolution on the initial image pixel matrix 320 with the uniform convolution kernel 402 to generate a uniformly corrected image matrix 404 that is the same dimensions as the initial image pixel matrix 320. The uniformly corrected image matrix 404 is converted into a visual format as a uniformly corrected image which may be inspected by a radiologist or a machine with computer-aided detection.

Figure 4B:
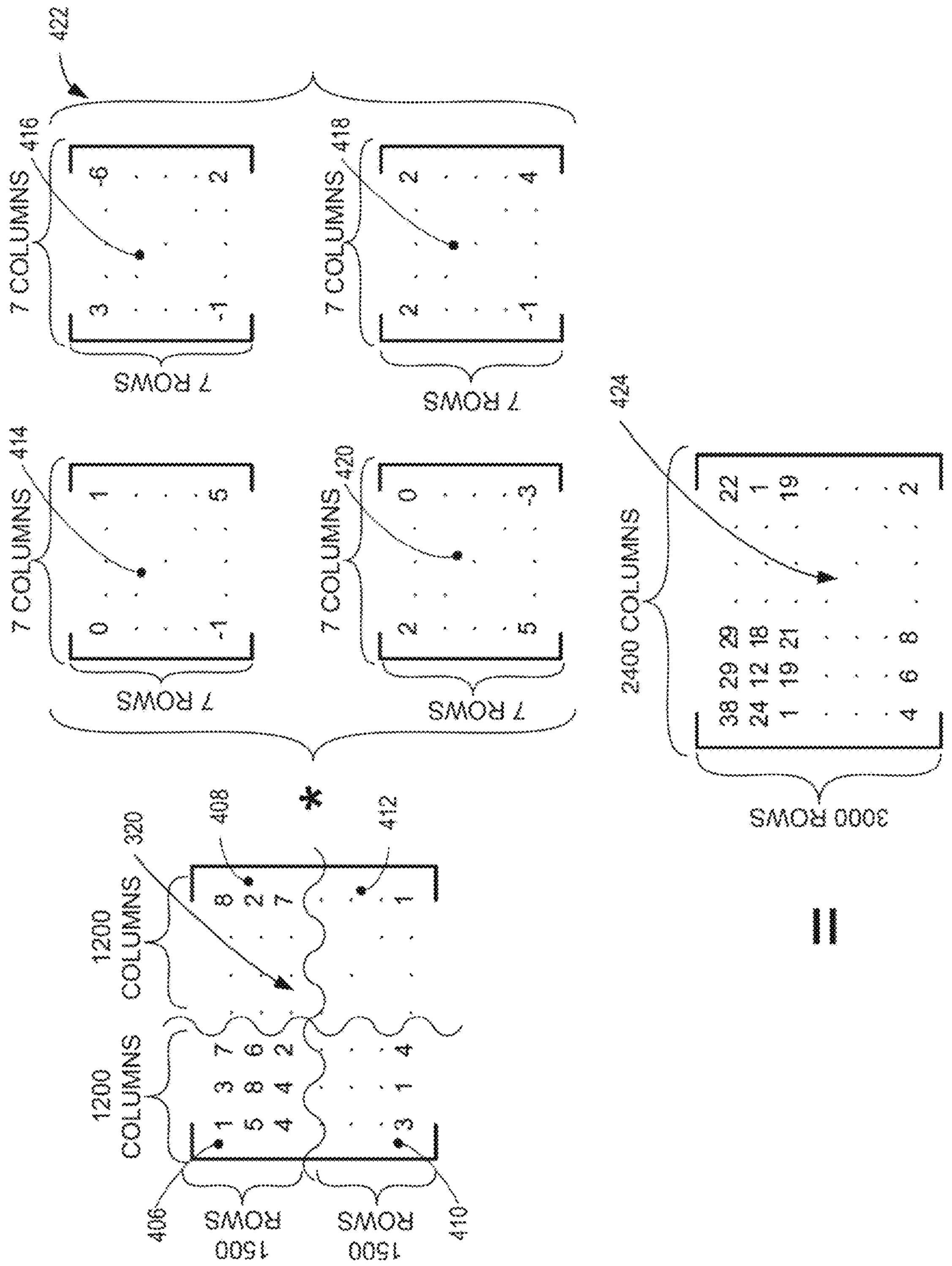
FIG. 4B illustrates a technique that uses a non-uniform set of local convolution kernels to sharpen the initial radiographic image captured by the medical imaging device to generate a locally sharpened image.

FIG. 4B illustrates a technique that uses a non-uniform set 422 of local convolution kernels 414, 416, 418, 420 to sharpen the initial image pixel matrix 320 that corresponds to the initial image 312 (FIG. 3) captured by the medical imaging device 100 (FIG. 1). The medical imaging device 100 performs image convolution on the initial image pixel matrix 320 with the non-uniform set 422 of local convolution kernels 414, 416, 418, 420 to generate a locally corrected image matrix 424. The locally corrected image matrix is converted into a visual format as a locally corrected image which may be inspected by a radiologist or a machine with computer-aided detection.

The example of FIG. 4B uses the same initial image pixel matrix 320 as FIG. 4A. However, the improved technique of FIG. 4B uses a plurality of different matrices rather than one matrix in image convolution. The techniques disclosed herein describe how the medical imaging device 100 is able to select (e.g., determine) which local convolution kernels 414, 416, 418, 420 from the non-uniform set 422 of local convolution kernels 414, 416, 418, 420 to apply to various portions of the initial image pixel matrix 320. As used herein, the non-uniform set 422 is a group (e.g., plurality) of local convolution kernels. In some examples, there may be more or fewer local convolution kernels than the four local convolution kernels 414, 416, 418, 420 that are shown in the example of FIG. 4B.

In the example of FIG. 4B, the initial image pixel matrix 320 is shown as divided into four regions 406, 408, 410, 412. However, in other examples, there may be more or fewer regions. The four regions 406, 408, 410, 412 of the example of FIG. 4B have dimensions of one thousand and two hundred columns (1,200) and one thousand and five hundred rows (1,500).

The medical imaging device 100 assigns the local convolution kernels 414, 416, 418, 420 to the regions 406, 408, 410, 412 of the initial image pixel matrix 320. For example, a first local convolution kernel 414 is assigned to a first region 406, a second local convolution kernel 416 is assigned to a second region 408, a third local convolution kernel 418 is assigned to a third region 410, and a fourth local convolution kernel 420 is assigned to a fourth region 412.

However, in other examples, different convolution kernel assignments may be selected by the medical imaging device 100. For example, the medical imaging device 100 may determine to use the first local convolution kernel 414 and the second local convolution kernel 416 for a left half and a right half of the initial image pixel matrix. In other examples, more local convolution kernels (such as nine local convolution kernels) may be used by the medical imaging device 100 to sharpen (e.g., correct, adjust, etc.) the initial image 312 (FIG. 3). After assigning the local convolution kernels 414, 416, 418, 420 to the regions 406, 408, 410, 412 of the initial image pixel matrix 320, the medical imaging device 100 performs image convolution to generate a locally corrected image matrix 424. By using local convolution kernels 414, 416, 418, 420, the medical imaging device 100 that uses the techniques described herein increases an accuracy and efficiency of a computing device.

Figure 4C:
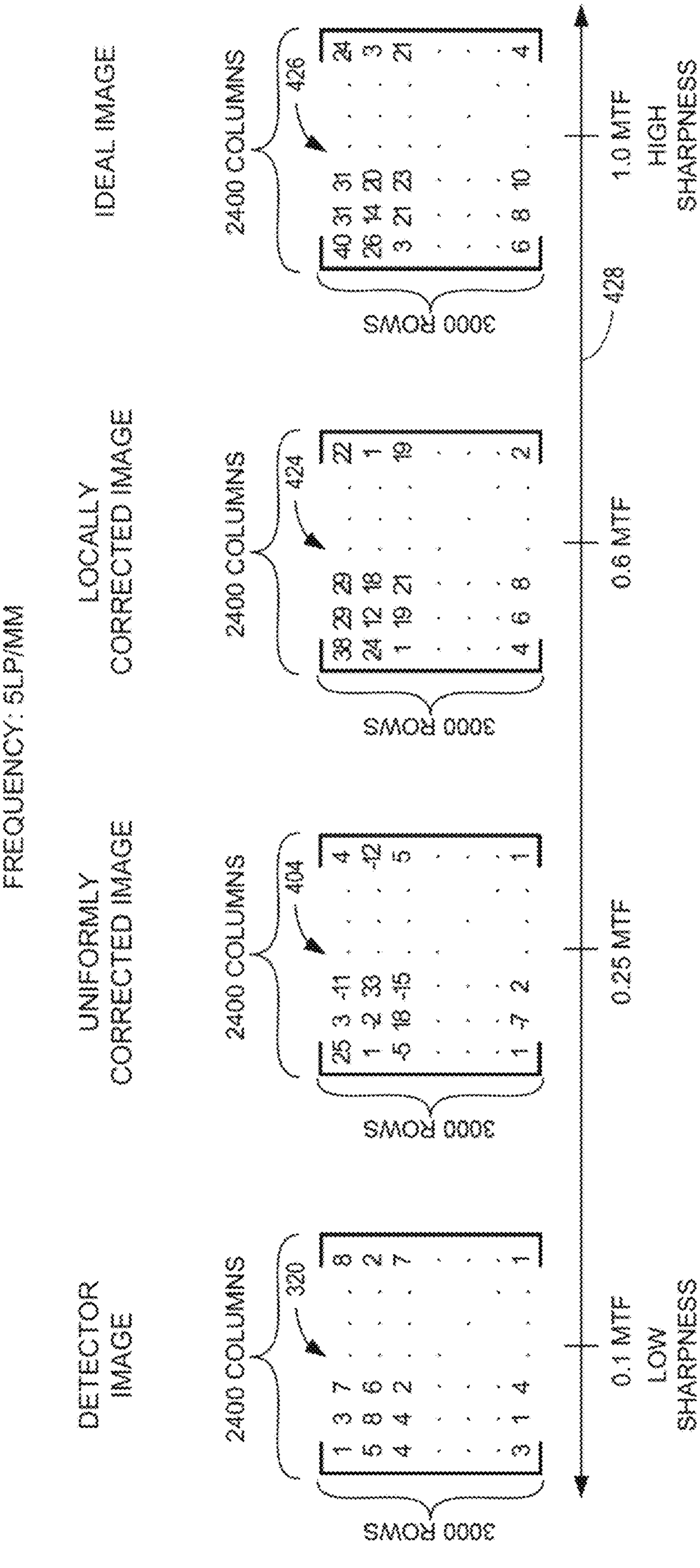
FIG. 4C compares modulation transfer function values for the initial radiographic image, the uniformly sharpened image, the locally sharpened image, and an ideal image.

FIG. 4C compares the initial image pixel matrix 320 (e.g., the pixels that represent the image captured by the detector 108), the uniformly corrected image matrix 404, the locally corrected image matrix 424, and an ideal image matrix 426 along a numerical line 428. The ideal image matrix 426 illustrates the pixel values that perfectly correspond to an image if there was no blurring due to the detector 108 (FIG. 1). The ideal image matrix 426 is at an ideal value of 1.0 MTF at all frequencies which corresponds to a perfect or ideal sharpness. "High" sharpness and "low" sharpness between 1.0 and 0.1 can vary based on frequency. For example, at a frequency of five line pairs per millimeter (5.0 lp/mm), the locally corrected image matrix 424 has a high sharpness value of 0.6 while the uniformly corrected image matrix 404 has a low sharpness value of 0.25. As shown in the example of FIG. 4C, the locally corrected image matrix 424 has an increased contrast of small details per high spatial frequencies and a removal of blurriness, which results in improved sharpness and clarity.

Figure 5A:
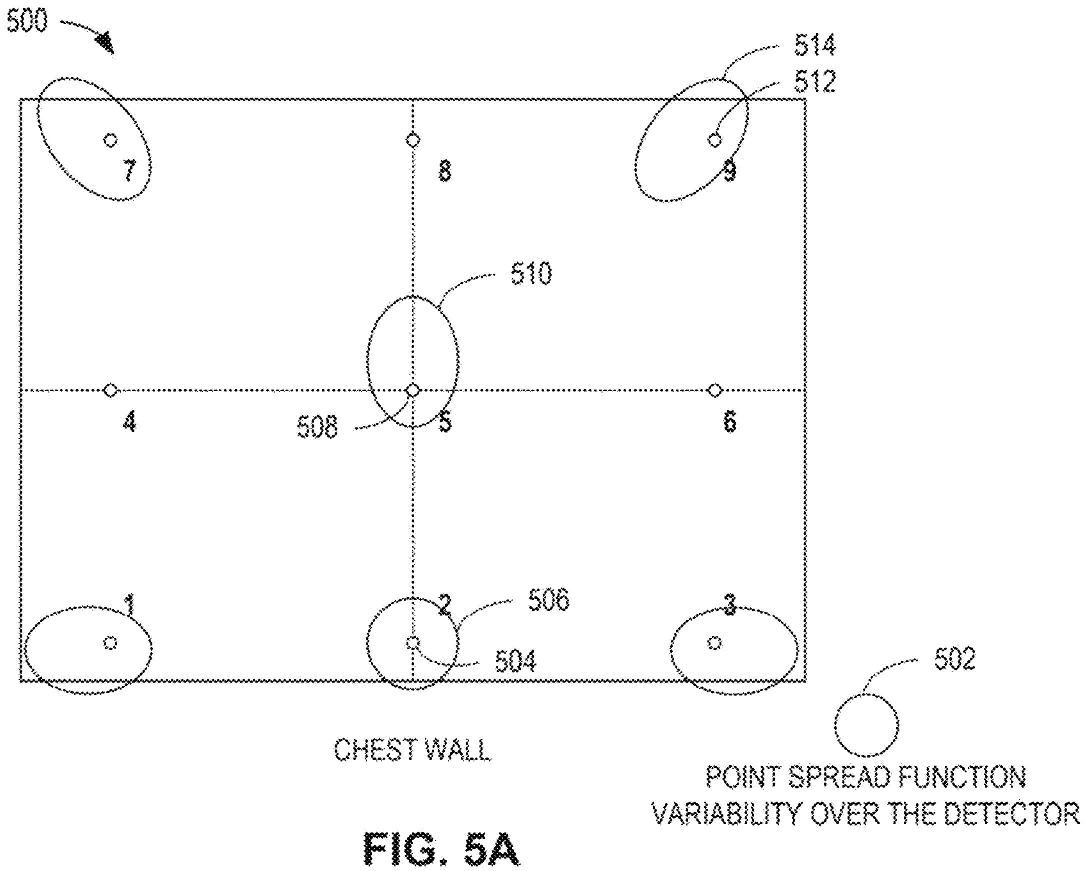
FIG. 5A illustrates point-spread values overlayed on initial detector positions on the detector.

FIG. 5A is a diagram 500 that overlays, in two dimensions, different positions of the detector 108 on an image highlighting a chest wall. In the example of FIG. 5A, there are nine different detector positions that can be exposed to portions of the beam 202 from the source 102. For ease of description, of the example nine detector positions, three detector positions are labeled as example locations of interest.

The example first location 504 corresponds to detector position 2, the example second location 508 corresponds to detector position 5, and the example third location 512 corresponds to detector position 9. The first location 504 has a corresponding first point spread function 506, the second location 508 has a corresponding second point spread function 510, and the third location 512 has a corresponding third point spread function 514. A standard point spread function 502 is illustrated as a circle.

While all nine detector positions have a corresponding point spread function due to the scintillation process described in connection with FIG. 3, three example point spread functions 506, 510, 514 are labeled in the example of FIG. 4. The example source 102 (FIG. 1) is aligned above the first location 504 (e.g., detector position 2). Due to the alignment of the source 102 (FIG. 1), the first point spread function 506 of the first location 504 (e.g., detector position 2) is circular and constrained. However, the third point spread function 514 of the third location 512 (e.g., detector position 9) is elliptical and not constrained because the beam 202 impacts the detector 108 at a certain angle of incidence at the third location 512 (e.g., detector position 9) that is different from the more direct incidence at the first location 504 (e.g., detector position 2). Due to the increased variability (e.g., increased size) in the third point spread function 514, an increased correction is used to sharpen the resulting image from pixels located near the third location 512. The increased correction used to sharpen the resulting image is increased in comparison to a level of correction to sharpen the resulting image from pixels located near the first location 504, which has a more constrained first point spread function 506. Therefore, the medical imaging device 100 uses different non-uniform convolution kernels (e.g., such as the non-uniform set 422 of local convolution kernels 414, 416, 418, 420 of FIG. 4B).

In some examples, the medical imaging device 100 is to measure a first point spread function value corresponding to a first location on the detector 108 (FIG. 2) and a second point spread function value corresponding to the second location on the detector 108 (FIG. 2). In such examples, the source 102 (FIG. 2) may be directly above the first location on the detector 108 (FIG. 2) and offset by a first distance above the second location on the detector 108 (FIG. 2). By determining the offset distance, the medical imaging device 100 estimates a difference in the first point spread function value and the second point spread function value.

For a three-dimensional image (3D) tomosynthesis image, as the source 102 (FIG. 2) rotates, the snapshot images taken at the various angles have their own corresponding point-spreads.

Figure 5B:
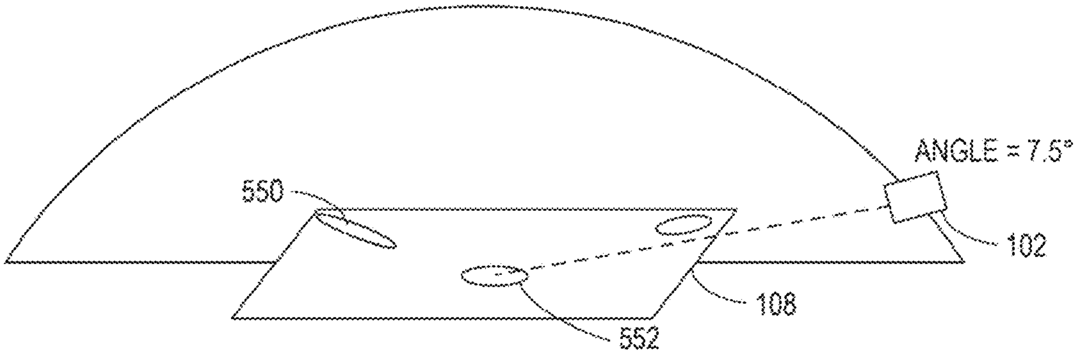
FIG. 5B illustrates a first angle between a source of the medical imaging device and a detector of the medical imaging device.

FIG. 5B illustrates a first angle between a source 102 of the medical imaging device 100 (FIG. 1) and a detector 108 of the medical imaging device (FIG. 1). The first angle in the example of FIG. 5B is seven and a half degrees (e.g., 7.5°). The source 102 is traveling around the detector 108 in DBT tomosynthesis. In DBT tomosynthesis, the source 102 takes multiple two-dimensional snapshots from different angles and generates a three-dimensional image. As shown in the example of FIG. 5B, a first point spread function 550 corresponds to a detector position farther away from the source 102 than a second point spread function 552. The second point spread function 552 is shown as more circular than the first point spread function 550. The first point spread function 550 is shown as more elliptical than the second point spread function 552.

Figure 5C:
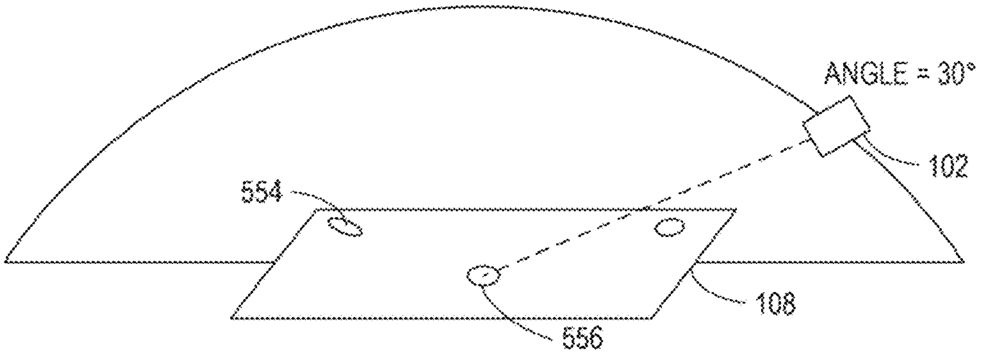
FIG. 5C illustrates a second angle between the source of the medical imaging device and the detector of the medical imaging device.

FIG. 5C illustrates a second angle between the source 102 of the medical imaging device (FIG. 1) and the detector 108 of the medical imaging device 100 (FIG. 1). The second angle in the example of FIG. 5C is thirty degrees (e.g., 30°). As shown in the example of FIG. 5C, a third point spread function 554 corresponds to a detector position farther away from the source 102 than a fourth point spread function 556. The fourth point spread function 556 is shown as more circular than the third point spread function 554. The third point spread function 554 is shown as more elliptical than the fourth point spread function 556. The first point spread function 550 of FIG. 5B is shown as more elliptical than the third point spread function 554 of FIG. 5C which corresponds to the first point spread function 550 of FIG. 5B being less accurate and the third point spread function 554 of FIG. 5C. Similarly, the second point spread function 552 of FIG. 5B is shown as more elliptical than the fourth point spread function 556 of FIG. 5C. As shown in the example of FIGS. 5B-5C, the amount of correction for the different regions of the detector 108 is based on the angle between the source 102 and the detector 108.

Figure 6A:
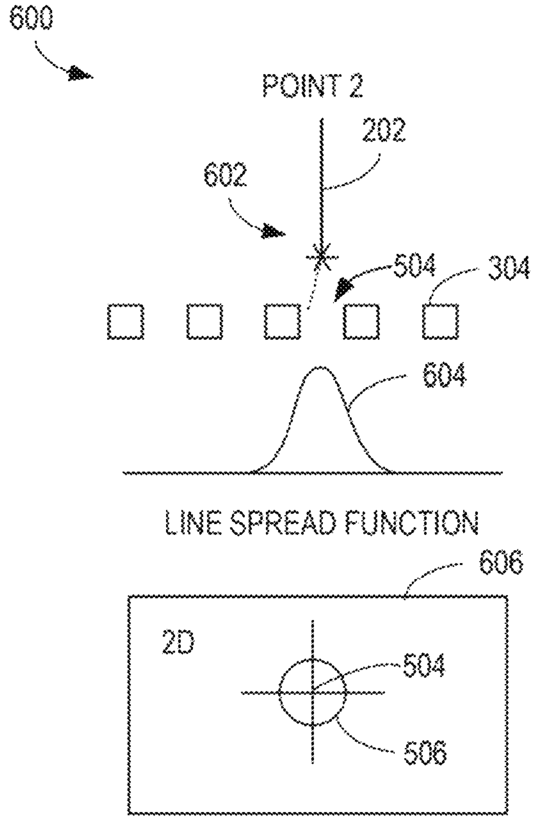
FIG. 6A illustrates a scintillation process and corresponding line spread function for detector position 2 of the detector of the medical imaging device.

FIG. 6A illustrates an example first scintillation process 600 and corresponding line spread function for detector position 2 of the detector 108 of the medical imaging device 100. The first location 504 (e.g., detector position 2) is shown directly underneath the beam 202. The example beam 202 is shown scintillating at interaction 602. At interaction 602, the beam 202 interacts with the example scintillator layer 302 (FIG. 3). Different portions of the scintillated particles travel to various ones of the photodiodes of the photodiode layer 304 (FIG. 3). In the example of FIG. 6A, a first scintillated particle is captured by the example photodiodes that correspond to detector position 2 (e.g., the first location 504 of FIG. 5A).

The example of FIG. 6A includes a first line spread function 604 which represent probability values of where the first scintillated particle impacted the photodiode layer 304 of the detector 108 (FIG. 1). In other words, the first line spread function 604 corresponds to a spread function that illustrates variation in where the first scintillated particle impacted the detector 108 (FIG. 1). The first line spread function 604 has a precision value that is determined by the amount of spread (e.g., variation). For example, a larger amount of spread (e.g., variation) corresponds to a less precise precision value. For example, a smaller amount of spread (e.g., variation) corresponds to a more precise precision value.

FIG. 6A includes a two-dimensional view 606 of the impacted particle on the photodiode layer 304 of the detector 108 (FIG. 1). In the two-dimensional view 606, the first line spread function 604 has a relatively circular line spread 506 that surrounds the example first location 504 which is determined as a center point (e.g., impact point).

Figure 6B:
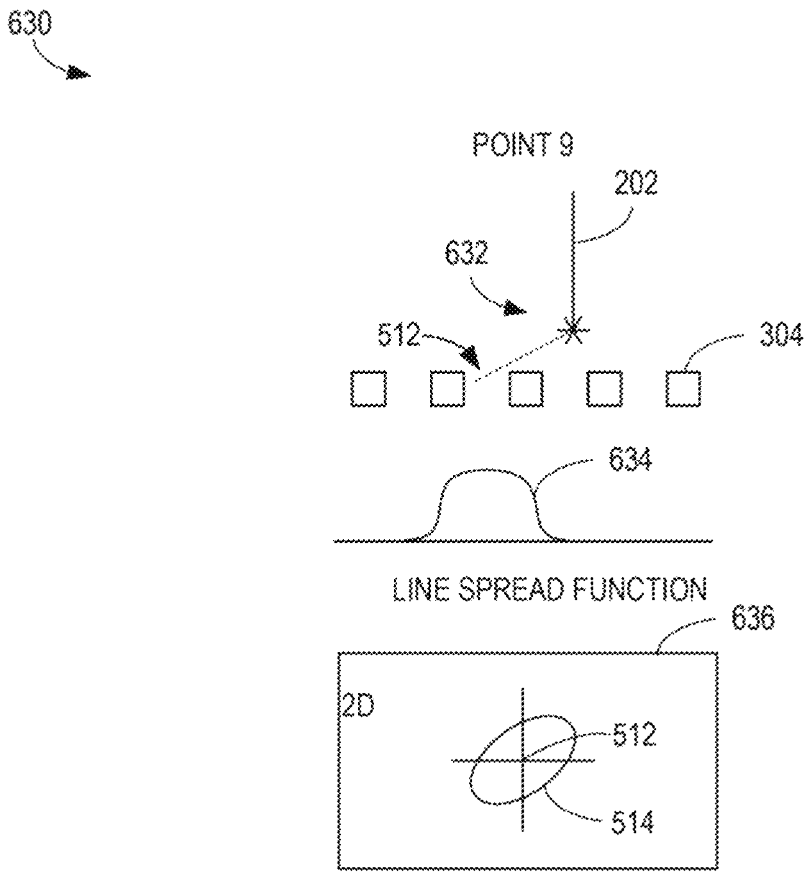
FIG. 6B illustrates a scintillation process and corresponding line spread function for detector position 9 of the detector of the medical imaging device.

FIG. 6B illustrates an example second scintillation process 630 and corresponding line spread function for detector position 9 of the detector 108 of the medical imaging device 100. The third location 512 (e.g., detector position 9) is shown offset from the beam 202. The example beam 202 is shown scintillating at interaction 632. At interaction 632, the beam 202 interacts with the example scintillator layer 302 (FIG. 3). Different portions of the scintillated particles travel to various ones of the photodiodes of the photodiode layer 304 (FIG. 3). In the example of FIG. 6B, a second scintillated particle is captured by the example photodiodes that correspond to detector position 9 (e.g., the third location 512 of FIG. 5A).

The example of FIG. 6B includes a second line spread function 634 which represent probability values of where the second scintillated particle impacted the photodiode layer 304 of the detector 108 (FIG. 1). In other words, the second line spread function 634 corresponds to a spread function that illustrates variation in where the second scintillated particle impacted the detector 108 (FIG. 1). The second line spread function 634 has a precision value that is determined by the amount of spread (e.g., variation). The example second line spread function 634 of FIG. 6B has a less precise precision value compared to the example first line spread function 604 of FIG. 6A. As shown in FIG. 6B, the second line spread function 634 has more variation than the first line spread function 604 of FIG. 6A.

FIG. 6B includes a two-dimensional view 636 of the impacted particle on the photodiode layer 304 of the detector 108 (FIG. 1). In the two-dimensional view 636, the second line spread function 636 has a relatively elliptical line spread 514 that surrounds the example third location 512 which is determined as a center point (e.g., impact point). Due to the increased variation (e.g., less precision) of the second line spread function 634, an image generated with pixel values of the third location 512 (FIG. 5A) and the first location 504 (FIG. 5A) includes some blur (e.g., lack of sharpness).

Figure 6C:
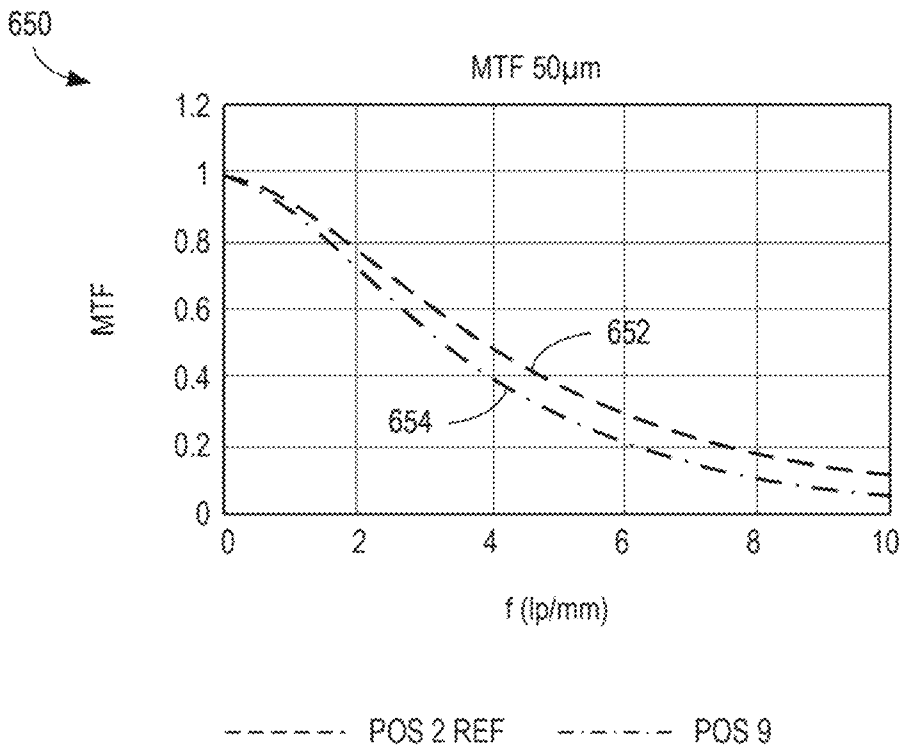
FIG. 6C illustrates a comparison between a modulation transfer function of detector position 2 and detector position 9.

FIG. 6C illustrates an example graph 650 that includes an example first modulation transfer function 652 that corresponds to the first location 504 of the detector 108 (e.g., detector position 2 as shown in the example of FIG. 5A) and an example second modulation transfer function 654 that corresponds to the third location 512 of the detector 108 (e.g., detector position 9 in the example of FIG. 5A). The modulation transfer functions 652, 654 are based on a beam emission (e.g., X-ray) of fifty (50) micrometers. The horizontal X-axis is a frequency which is represented as a number of distinguishable line pairs per millimeter (lp/mm). The vertical Y-axis is an MTF value which quantifies an ability of the detector 108 to accurately convert the received beam 202 into electrical signals that convey information about an object, including contrast in and around the object to form a resulting image. A perfect (e.g., ideal) MTF value is 1.0 at all frequencies of the horizontal X-axis, while a value of less than 1.0 is less sharp (e.g., decreased sharpness, increased blurriness). As seen in the graph 650 of FIG. 6C, the first modulation transfer function 652 is sharper than the second modulation transfer function 654 as seen by the MTF values of the first modulation transfer function 652 being larger than the second modulation transfer function 654 along the different frequencies (e.g., 2 line pairs per millimeter, 4 line pairs per millimeter, 6 line pairs per millimeter, etc.).

The techniques disclosed herein use the medical imaging device circuitry 700 (FIG. 7) to sharpen a radiographic image generated (e.g., created, produced, captured) by the medical imaging device 100 (FIG. 1). As shown in FIG. 6C, there is a different level of correction (e.g., compensation) for the first modulation transfer function 652 and the second modulation transfer function 654 to increase the sharpness (e.g., clarity, precision). The medical imaging device circuitry 700 uses sharpening algorithms with an adaptive local convolution kernel, rather than a single uniform convolution kernel. In certain examples, the adaptive convolution kernel is implemented as a library or set of local convolution kernels to determine an individualized amount of correction to apply to the image for a particular area of the detector 108.

By using a library of local convolution kernels (e.g., a non-uniform set of local convolution kernels corresponding to different detector locations, beam angles, etc.), the medical imaging device 100 (FIG. 1) more accurately accounts for the variability of the various nine detector positions of the detector 108 (FIG. 1). In other examples, the adaptive convolution kernel is implemented as a convolution kernel function (e.g., an adaptive or dynamic local convolution kernel function) that is used to dynamically generate localized convolution kernels for different areas of the detector 108 based on one or more parameters including angle, position, dose, etc., for the detector 108.

Figure 7:
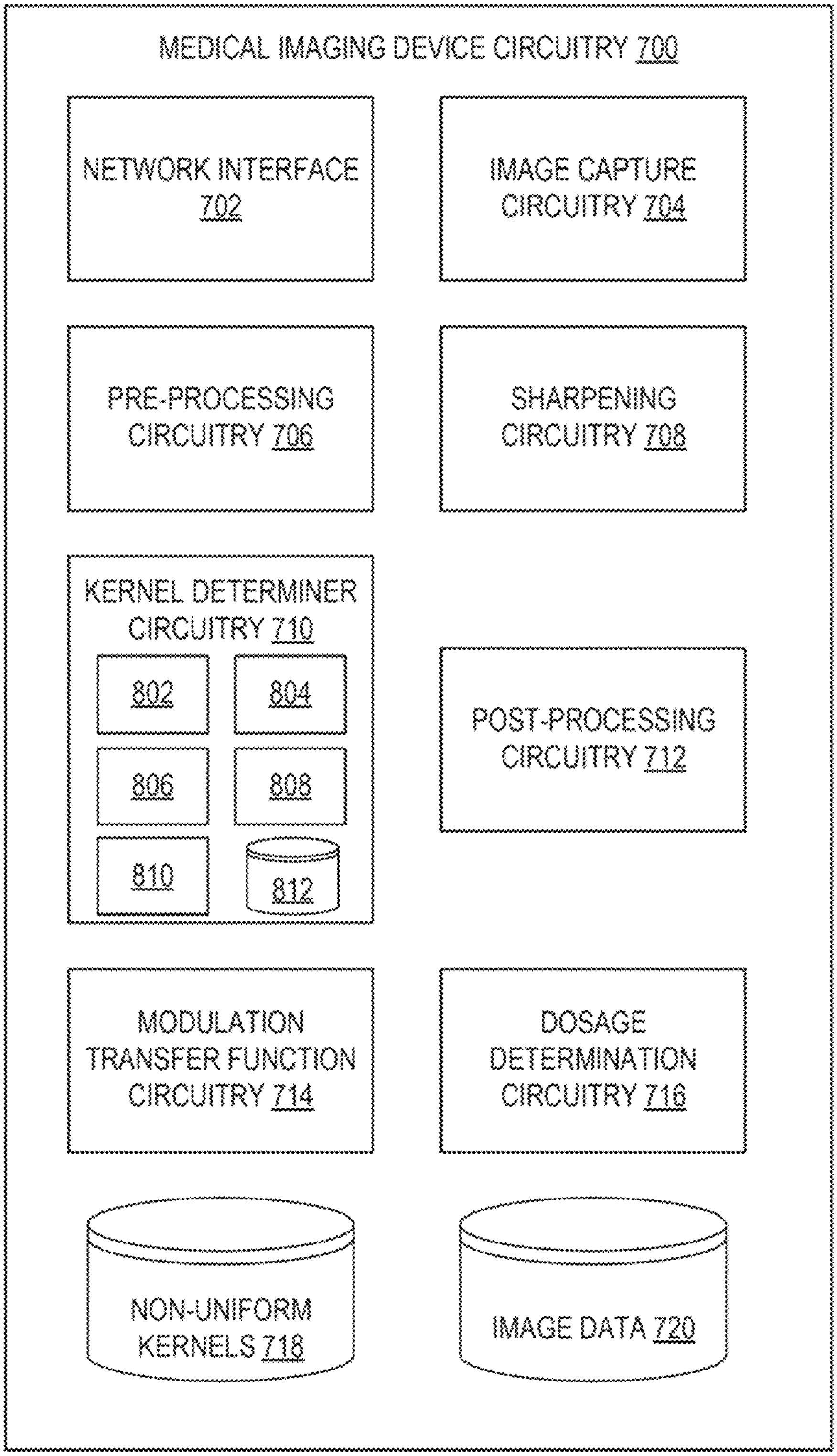
FIG. 7 is a block diagram of an example implementation of medical imaging device circuitry that is used to operate the medical imaging device of FIG. 1.
Figure 8:
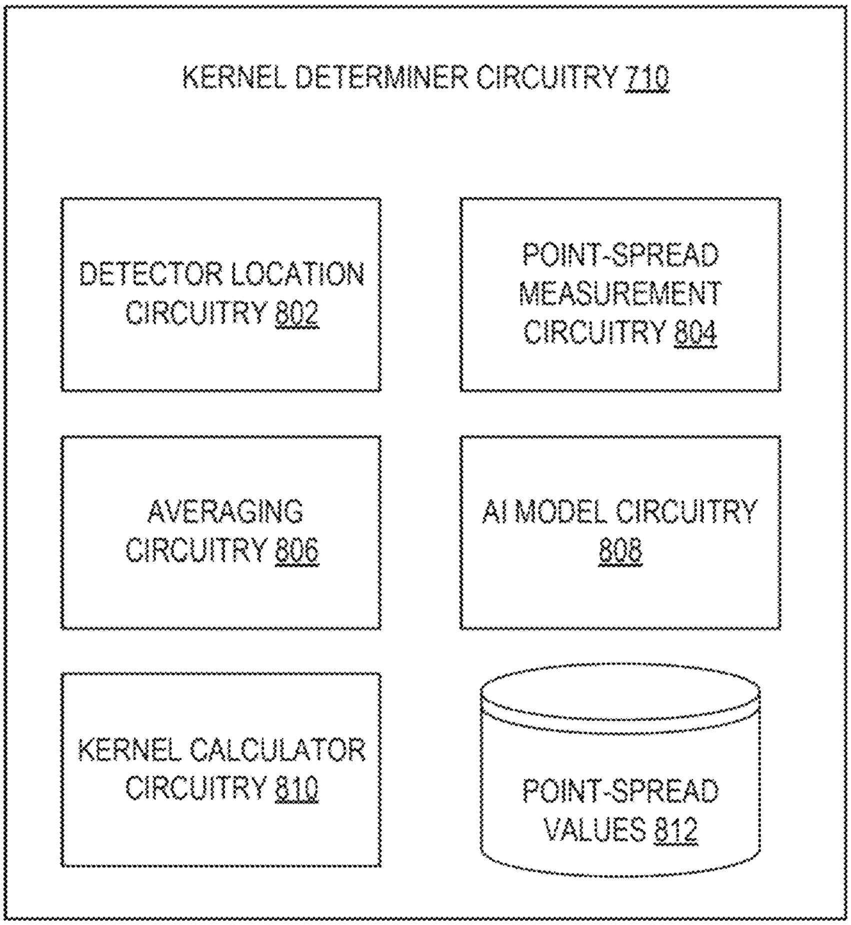
FIG. 8 is a block diagram of an example implementation of kernel determiner circuitry that is used by the medical imaging device circuitry of FIG. 7.

FIG. 7 is a block diagram of an example implementation of the medical imaging device circuitry 700 to operate the medical imaging device 100 of FIG. 1. FIG. 8 is a block diagram of an example implementation of the kernel determiner circuitry 710 of FIG. 7 to determine the non-uniform set of local convolution kernels. The medical imaging device circuitry 700 of FIG. 7 and/or the kernel determiner circuitry 710 of FIG. 8 may be instantiated (e.g., creating an instance of, bring into being for any length of time, materialize, implement, etc.) by programmable circuitry such as a Central Processor Unit (CPU) executing first instructions. Additionally or alternatively, the medical imaging device circuitry 700 of FIG. 7 and/or the kernel determiner circuitry 710 of FIG. 8 may be instantiated (e.g., creating an instance of, bring into being for any length of time, materialize, implement, etc.) by (i) an Application Specific Integrated Circuit (ASIC) and/or (ii) a Field Programmable Gate Array (FPGA) structured and/or configured in response to execution of second instructions to perform operations corresponding to the first instructions. It should be understood that some or all of the circuitry of FIGS. 7-8 may, thus, be instantiated at the same or different times. Some or all of the circuitry of FIGS. 7-8 may be instantiated, for example, in one or more threads executing concurrently on hardware and/or in series on hardware. Moreover, in some examples, some or all of the circuitry of FIGS. 7-8 may be implemented by microprocessor circuitry executing instructions and/or FPGA circuitry performing operations to implement one or more virtual machines and/or containers.

The medical imaging device circuitry 700 includes an example network interface 702, example image capture circuitry 704, example pre-processing circuitry 706, example sharpening circuitry 708, example kernel determiner circuitry 710, example post-processing circuitry 712, example modulation transfer function circuitry 714, example dose determination circuitry 716, an example non-uniform kernels data store 718, and an example image data store 720.

Turning briefly to FIG. 8, the example kernel determiner circuitry 710 of FIG. 8 includes example detector location circuitry 802, example point-spread measurement circuitry 804, example averaging circuitry 806, example AI model circuitry 808, example kernel calculator circuitry 810, and an example point-spread values data store 812. In some examples, the medical imaging device circuitry 700 directly includes the example detector location circuitry 802, example point-spread measurement circuitry 804, example averaging circuitry 806, example AI model circuitry 808, example kernel calculator circuitry 810, and an example point-spread values data store 812. In other examples, one or more of the sharpening circuitry 708, the kernel determiner circuitry 710, the modulation transfer function circuitry 714, and the dose determination circuitry 716 can be distributed between the medical imaging device 100 and other computing circuitry.

Returning to FIG. 7, the example network interface 702 is to receive, from a computer (e.g., a workstation operated by a radiologist, automated according to protocol, etc.), instructions that include specific radiographic images to be captured. After the images are captured and processed by the medical imaging device 100 (FIG. 1), the example network interface 702 transmits the radiographic images from the medical imaging device 100 (FIG. 1) to an external system (e.g., computer, display, user interface, storage at another device, etc.). The radiographic images are examined by the external system.

The image capture circuitry 704 of the medical imaging device circuitry 700 is to perform capture of the radiographic images. The example radiographic images include different types (e.g., X-ray, flat detector images, cone-beam computed tomography images, and tomosynthesis images), different doses (e.g., an X-ray of a first strength such as ten micrograys (e.g., 10 μGy), an X-ray of a second dose such as twenty micrograys (e.g., 20 μGy)), and different dimensions (e.g., two-dimensional (2-D), three-dimensional (3-D)). The image capture circuitry 704 is to activate (e.g., operate) the source 102 (FIG. 2). After the selected source 102 (FIG. 2) is activated and emits the beam 202 (FIG. 2), the image capture circuitry 704 saves the image data as an initial image 312 (FIG. 3) to the example image data store 720.

The example pre-processing circuitry 706 is to apply preliminary corrections to the initial image 312 (FIG. 3). The example pre-processing circuitry 706 performs at least one of a noise filter, a gain filter, and a filter that removes bad pixels (e.g., pixels that are defective, pixels that transmit white light, pixels that do not transmit light). After performing the preprocessing on the initial image, the pre-processing circuitry 706 generates a pre-processed image from the initial image 312 (FIG. 3). In some examples, the medical imaging device circuitry 700 performs sharpening on the initial image 312 (FIG. 3) before pre-processing occurs. In other examples, the medical imaging device circuitry 700 performs sharpening on a pre-processed image.

The example sharpening circuitry 708 performs a digital correction on the radiographic image. One example method of a digital correction is that the sharpening circuitry 708 accesses at least one determined convolution kernel (e.g., multiple local convolution kernels, a library of convolution kernels that correspond to different detector positions and angles, a non-uniform set of convolution kernels, etc.) from the example kernel determiner circuitry 710. The example sharpening circuitry 708 applies the at least one determined convolution kernel by performing convolution with the initial image pixel matrix 320 (FIG. 3). By applying the at least one determined convolution kernel, the sharpening circuitry 708 sharpens the initial image pixel matrix 320 (FIG. 4C) to generate a locally corrected image matrix 424 (FIG. 4C) that is sharper than a uniformly corrected image matrix 404 (FIG. 4C). In some examples, in addition to applying the at least one local convolution kernel, the sharpening circuitry 708 compensates for noise by using a sharpening algorithm (e.g., the GE HealthCare Fine View™ sharpening algorithm, etc.) that uses a Wiener filter. After applying the at least one local convolution kernel, the sharpening circuitry 708 transmits the locally corrected image to the post-processing circuitry 712. In some examples, the sharpening circuitry 708 performs filtering in Fourier space or artificial intelligence methods in performing a digital correction of the radiographic image (e.g., local spatial filtering such as using at least one local convolution kernel/kernel function, model, etc.).

The example kernel determiner circuitry 710 adaptively determines which local convolution kernel from a library of convolution kernels to apply to specific portions of the initial image pixel matrix 320 (FIG. 4B). For example, due to the various detector locations, the amount of compensation to reach an ideal sharpness is different for the various positions, so an individually selected convolution kernel more accurately compensates for detector variation (e.g., detector scatter). Further details of the kernel determiner circuitry 710 are described in connection with FIG. 8. In some examples, the kernel determiner circuitry 710 uses a continuously variable convolution kernel based on a position of the detector 108.

The post-processing circuitry 712 is to perform post-processing on the radiographic image. The post-processing circuitry 712 performs the post-processing on the radiographic image after the convolution kernel has been applied which further sharpens the radiographic image. For example, a first post-processing technique is contrast enhancement. A second post-processing technique is denoising. The post-processing circuitry 712 uses post-processing to improve the image look after kernel convolution and before image display.

Figure 11:
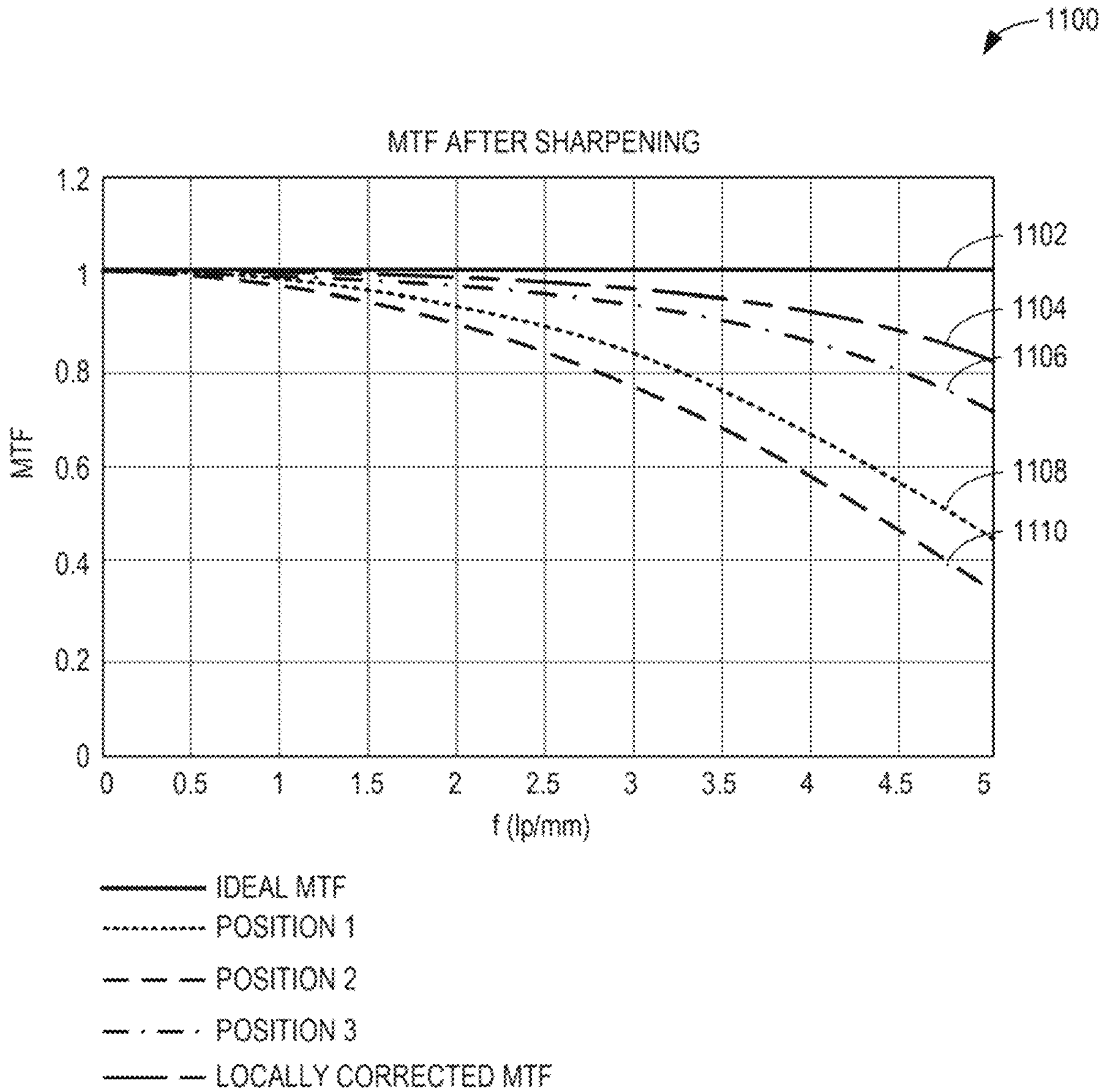
FIG. 11 is an example graph that compares modulation transfer functions for multiple detector positions and a locally corrected modulation transfer function for the multiple detector positions.
Figure 12:
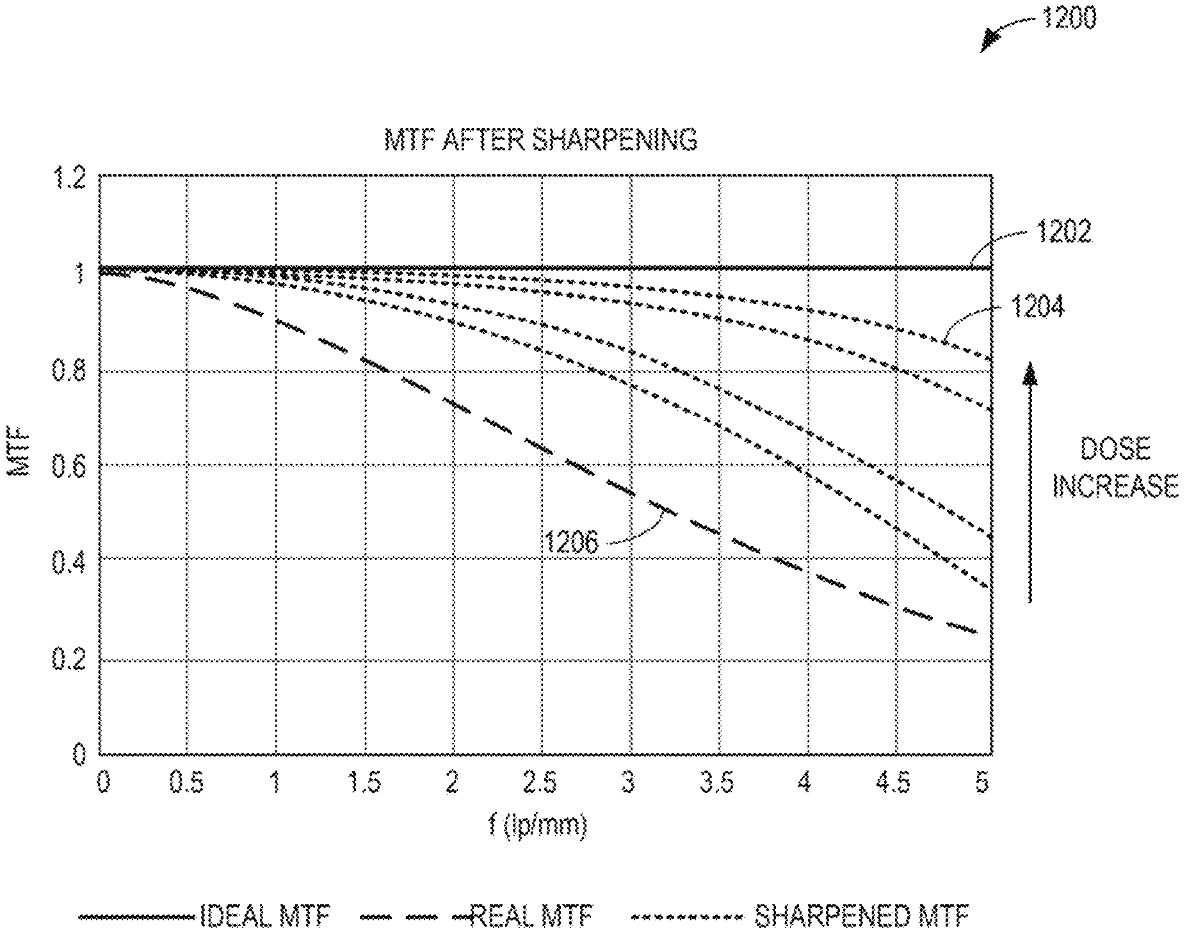
FIG. 12 is an example graph comparing the various modulation transfer function for multiple dose levels.

The modulation transfer function circuitry 714 generates graphs such as the graphs of FIGS. 6C, 11, and 12. The modulation transfer function circuitry 714 is to measure the discernable line pairs in the image and to measure the MTF. By measuring the MTF, the modulation transfer function circuitry 714 measures the contrast, clarity, and sharpness in the radiographic images. In some examples, the kernel determiner circuitry 710 uses the graphs and measurements of the modulation transfer function circuitry 714 to calibrate the medical imaging device 100. These local convolution kernels are to be applied for the different detector locations in two-dimensional images, the different snapshot images in three-dimensional images, and at various doses. In some examples, the modulation transfer function circuitry 714 is to measure the increase in the MTF based on the specific local convolution kernels. In some examples, the modulation transfer function circuitry 714 calculates specific MTF values for various regions in a piece-wise manner. In such examples, the modulation transfer function circuitry 714 iterates (e.g., loops) over the various regions of the image until the entire image is corrected. In some examples, the modulation transfer function circuitry 714 retrieves MTF in a piece-wise process based on Richardson-Lucy deconvolutions or Wiener filtering.

In some examples, calibration to determine the MTF for the detector occurs before and/or between patient exams on the medical imaging device 100. In other examples, the medical imaging device 100 is calibrated at manufacture before being released to a healthcare facility. The MTF can be determined based on imaging a known reference object, using a model of the detector, etc.

The dose determination circuitry 716 determines a dose level (e.g., dose value) used in generating the radiographic image. Differing dose levels correspond to different kernel strengths that are to be used to sharpen the radiographic image. For example, a dose value such as twenty micrograys (e.g., 20 μGy) of radiation in an X-ray only requires a small adjustment (e.g., a small compensation) to sharpen the image. Alternatively, a dose value such as one hundred and fifty micrograys (e.g., 150 μGy) of radiation in an X-ray requires a larger adjustment (e.g., a larger compensation). For example, at a frequency of four line pairs per millimeter (4 lp/mm), a small kernel adjustment is 1.05 and a large kernel adjustment is 2.0.

In some examples, the medical imaging device circuitry 700 includes means for transmitting images to a central computer which may be implemented by the network interface 702. For instance, the network interface 702 may be instantiated by the example programmable circuitry 1312 of FIG. 13, the example microprocessor 1400 of FIG. 14, or the FPGA circuitry 1500 of FIG. 15 executing machine executable instructions or operations corresponding to the machine readable instructions such as those implemented by at least blocks 906, 924 of FIG. 9.

In some examples, the medical imaging device circuitry 700 includes means for capturing images which may be implemented by the image capture circuitry 704. For instance, the image capture circuitry 704 may be instantiated by the example programmable circuitry 1312 of FIG. 13, the example microprocessor 1400 of FIG. 14, or the FPGA circuitry 1500 of FIG. 15 executing machine executable instructions or operations corresponding to the machine readable instructions such as those implemented by at least blocks 908, 910, 912, 914 of FIG. 9 and block 1004 of FIG. 10.

In some examples, the medical imaging device circuitry 700 includes means for performing pre-processing on initial images which may be implemented by the pre-processing circuitry 706. For instance, the pre-processing circuitry 706 may be instantiated by the example programmable circuitry 1312 of FIG. 13, the example microprocessor 1400 of FIG. 14, or the FPGA circuitry 1500 of FIG. 15 executing machine executable instructions or operations corresponding to the machine readable instructions such as those implemented by at least block 916 of FIG. 9.

In some examples, the medical imaging device circuitry 700 includes means for performing a sharpening algorithm on images which may be implemented by the sharpening circuitry 708. For instance, the sharpening circuitry 708 may be instantiated by the example programmable circuitry 1312 of FIG. 13, the example microprocessor 1400 of FIG. 14, or the FPGA circuitry 1500 of FIG. 15 executing machine executable instructions or operations corresponding to the machine readable instructions such as those implemented by at least block 920 of FIG. 9.

In some examples, the medical imaging device circuitry 700 includes means for generating an adaptive continuously variable local convolution kernel function or a non-uniform set of local convolution kernels which may be implemented by the kernel determiner circuitry 710. For instance, the kernel determiner circuitry 710 may be instantiated by the example programmable circuitry 1312 of FIG. 13, the example microprocessor 1400 of FIG. 14, or the FPGA circuitry 1500 of FIG. 15 executing machine executable instructions or operations corresponding to the machine readable instructions such as those implemented by at least block 918 of FIG. 9 and blocks 1002, 1006, 1008, 1010, 1012, 1014, 1016 of FIG. 10.

In some examples, the medical imaging device circuitry 700 includes means for performing post-processing on the corrected image which may be implemented by the post-processing circuitry 712. For instance, the post-processing circuitry 712 may be instantiated by the example programmable circuitry 1312 of FIG. 13, the example microprocessor 1400 of FIG. 14, or the FPGA circuitry 1500 of FIG. 15 executing machine executable instructions or operations corresponding to the machine readable instructions such as those implemented by at least block 922 of FIG. 9.

In some examples, the medical imaging device circuitry 700 includes means for determining a dose of a mammographic image which may be implemented by the dose determination circuitry 716. For instance, the dose determination circuitry 716 may be instantiated by the example programmable circuitry 1312 of FIG. 13, the example microprocessor 1400 of FIG. 14, or the FPGA circuitry 1500 of FIG. 15 executing machine executable instructions or operations corresponding to the machine readable instructions such as those implemented by at least blocks 906, 914 of FIG. 9.

FIG. 8 describes an example implementation of the kernel determiner circuitry 710 of FIG. 7. The example kernel determiner circuitry 710 includes example detector location circuitry 802, example point-spread measurement circuitry 804, example averaging circuitry 806, example AI model circuitry 808, example kernel calculator circuitry 810, and an example point-spread values data store 812.

The example detector location circuitry 802 determines a plurality of detector locations. For example, in the example of FIG. 5A, there are nine detector locations. The example detector location circuitry 802 determines where the source 102 (FIG. 1) is located above the detector 108 (FIG. 1). In the example of FIG. 5A, the source 102 (FIG. 1) is aligned above the first location 504 of FIG. 5A (e.g., detector position 2). In other examples, the source 102 (FIG. 1) may be initially aligned above the second location 508 of FIG. 5A (e.g., detector position 5). The point spread functions that correspond from a test image with the different alignment are different than as shown in FIG. 5A. By determining the detector locations, the detector location circuitry 802 has calibration information that may be used to further refine an amount of compensation.

The example point-spread measurement circuitry 804 measures the point spread function value associated with ones of the plurality of detector locations. The example point-spread measurement circuitry 804 stores the point spread function values corresponding to the plurality of detector locations in the example point-spread values data store 812.

In some examples, the point-spread measurement circuitry 804 receives point spread function values and measurements from other medical imaging devices such as an identical medical imaging device in a separate hospital. In some examples, a technician may manually measure the various point spread functions on the detector 108. In some examples, various machines may have calibration tables for the point spread function values that are stored in an online data store. The point-spread measurement circuitry 804 may use the network interface 702 of the medical imaging device circuitry 700 to access online calibration tables stored in the online data store.

The example averaging circuitry 806 averages the various point-spread measurements that are stored in the point-spread values data store 812. By averaging the at least two saved point spread function values, the averaging circuitry 806 increases a precision of an average point spread function value. For example, if the measured point spread function value of a first detector location at a first time is one hundred and fifty micrometers (e.g., 150 μm) and the point spread function value of the same first detector location at a second time is three hundred and fifty micrometers (e.g., 350 μm), the average of the two point spread function values is two hundred and fifty micrometers (e.g., 250 μm). In the example of FIG. 5A, there are nine detector locations, and therefore the example averaging circuitry 806 determines nine average point-spread values. In some examples, such as where there is only one test image, the averaging circuitry 806 does not average the point-spread values, and instead saves the point-spread values for use by the kernel calculator circuitry 810.

The example AI model circuitry 808 implements a machine learning (ML) model and/or an artificial intelligence (AI) model which may perform any of the functions of the example point-spread measurement circuitry 804, the example averaging circuitry 806, and/or the kernel calculator circuitry 810. By using an AI/ML model, the AI model circuitry 808 is to make predictions that improve with further training data.

In some examples, the AI model circuitry 808 implements the AI model to infer the locations of the point spread function values. In some examples, the AI model circuitry 808 implements the AI model that uses the average point spread function values as inputs and generate the non-uniform kernel set as output with information for the sharpening circuitry 708 (FIG. 7) to selectively apply ones of the local kernels in the generated non-uniform kernel set. In some examples, the AI model circuitry 808 implements the AI model is used to generate an AI point spread function value used in calibrating the local kernel.

Artificial intelligence (AI), including machine learning (ML), deep learning (DL), and/or other artificial machine-driven logic, enables machines (e.g., computers, logic circuits, etc.) to use a model to process input data to generate an output based on patterns and/or associations previously learned by the model via a training process. For instance, the model may be trained with data to recognize patterns and/or associations and follow such patterns and/or associations when processing input data such that other input(s) result in output(s) consistent with the recognized patterns and/or associations.

Many different types of machine learning models and/or machine learning architectures exist. In examples disclosed herein, a convolutional model is used. Using a convolutional model enables image sharpening by taking an initially blurry image using a sharpening term. In examples disclosed herein, a deconvolutional model is used. Using a deconvolutional model enables image sharpening by taking an initially blurry image and removing blurry components (e.g., removing a blurring kernel).

In general, implementing a ML/AI system involves two phases, a learning/training phase and an inference phase. In the learning/training phase, a training algorithm is used to train a model to operate in accordance with patterns and/or associations based on, for example, training data. In general, the model includes internal parameters that guide how input data is transformed into output data, such as through a series of nodes and connections within the model to transform input data into output data. Additionally, hyperparameters are used as part of the training process to control how the learning is performed (e.g., a learning rate, a number of layers to be used in the machine learning model, etc.). Hyperparameters are defined to be training parameters that are determined prior to initiating the training process.

Different types of training may be performed based on the type of ML/AI model and/or the expected output. For example, supervised training uses inputs and corresponding expected (e.g., labeled) outputs to select parameters (e.g., by iterating over combinations of select parameters) for the ML/AI model that reduce model error. As used herein, labelling refers to an expected output of the machine learning model (e.g., a classification, an expected output value, etc.) Alternatively, unsupervised training (e.g., used in deep learning, a subset of machine learning, etc.) involves inferring patterns from inputs to select parameters for the ML/AI model (e.g., without the benefit of expected (e.g., labeled) outputs).

In examples disclosed herein, ML/AI models are trained using stochastic gradient descent. However, any other training algorithm may additionally or alternatively be used. In examples disclosed herein, training is performed until an acceptable amount of error is achieved. In examples disclosed herein, training is performed remotely at a central facility (e.g., a manufacturer of the medical imaging devices 100). In some examples, training is performed locally at the healthcare facility. Training is performed using hyperparameters that control how the learning is performed (e.g., a learning rate, a number of layers to be used in the machine learning model, etc.).

Training is performed using training data. In examples disclosed herein, the training data originates from locally generated data. Because supervised training is used, the training data is labeled. Labeling is applied to the training data by a radiologist.

Once training is complete, the model is deployed for use as an executable construct that processes an input and provides an output based on the network of nodes and connections defined in the model. The model may then be executed by the AI model circuitry 808.

Once trained, the deployed model may be operated in an inference phase to process data. In the inference phase, data to be analyzed (e.g., live data) is input to the model, and the model executes to create an output. This inference phase can be thought of as the AI “thinking” to generate the output based on what it learned from the training (e.g., by executing the model to apply the learned patterns and/or associations to the live data). In some examples, input data undergoes pre-processing before being used as an input to the machine learning model. Moreover, in some examples, the output data may undergo post-processing after it is generated by the AI model to transform the output into a useful result (e.g., a display of data, an instruction to be executed by a machine, etc.).

In some examples, output of the deployed model may be captured and provided as feedback. By analyzing the feedback, an accuracy of the deployed model can be determined. If the feedback indicates that the accuracy of the deployed model is less than a threshold or other criterion, training of an updated model can be triggered using the feedback and an updated training data set, hyperparameters, etc., to generate an updated, deployed model.

The example kernel calculator circuitry 810 calculates a convolution kernel value based on the average point-spread values. For example, a larger point-spread value corresponds to a larger compensation and a smaller point-spread value corresponds to a smaller compensation. The example kernel calculator circuitry 810 computes a plurality of convolution kernels and stores the convolution kernels in the non-uniform kernels data store 718. In some examples, the kernel calculator circuitry 810 computes the plurality of convolution kernels based on geometric principles (e.g., an angle between the source 102 (FIG. 1) and the detector 108 (FIG. 1)). For example, the kernel calculator circuitry 810 generates a convolution kernel for each angle (e.g., 9 degrees, 10 degrees, 11 degrees, etc.) such as in FIGS. 5B-5C. In some examples, the kernel calculator circuitry 810 interpolates convolution kernel values between the various angles (e.g., 9.1 degrees, 9.2 degrees, etc.). In some examples, the kernel calculator circuitry 810 uses the AI model circuitry 808 to perform AI inference to interpolate the convolution kernel values.

In other examples, the kernel calculator circuitry 810 computes the plurality of local kernels based on the positions of the detector 108 (FIG. 1) such as the first location 504 (FIG. 5A), the second location 508 (FIG. 5A) and the third location 512 (FIG. 5A). In some examples, the kernel calculator circuitry 810 interpolates between the locations of the detector 108 (FIG. 1).

In some examples, the kernel calculator circuitry 810 interpolates the local convolution kernels (e.g., selects convolution kernels from the library) based on dose as determined by the example dose determination circuitry 716 (FIG. 7).

The example point-spread values data store 812 stores the individual point-spread values and the averaged point-spread values that correspond to the various detector locations.

While an example manner of implementing the medical imaging device circuitry 700 of FIG. 7 is illustrated in FIG. 7, one or more of the elements, processes, and/or devices illustrated in FIG. 7 may be combined, divided, re-arranged, omitted, eliminated, and/or implemented in any other way. Further, the example network interface 702, example image capture circuitry 704, example pre-processing circuitry 706, example sharpening circuitry 708, example kernel determiner circuitry 710, example post-processing circuitry 712, example modulation transfer function circuitry 714, example dose determination circuitry 716, and/or, more generally, the example medical imaging device circuitry 700 of FIG. 7, may be implemented by hardware alone or by hardware in combination with software and/or firmware. Thus, for example, any of the example network interface 702, example image capture circuitry 704, example pre-processing circuitry 706, example sharpening circuitry 708, example kernel determiner circuitry 710, example post-processing circuitry 712, example modulation transfer function circuitry 714, example dose determination circuitry 716, and/or, more generally, the example medical imaging device circuitry 700, could be implemented by programmable circuitry in combination with machine readable instructions (e.g., firmware or software), processor circuitry, analog circuit(s), digital circuit(s), logic circuit(s), programmable processor(s), programmable microcontroller(s), graphics processing unit(s) (GPU(s)), digital signal processor(s) (DSP(s)), ASIC(s), programmable logic device(s) (PLD(s)), and/or field programmable logic device(s) (FPLD(s)) such as FPGAs. Further still, the example medical imaging device circuitry 700 of FIG. 7 may include one or more elements, processes, and/or devices in addition to, or instead of, those illustrated in FIG. 7, and/or may include more than one of any or all of the illustrated elements, processes and devices.

Figure 9:
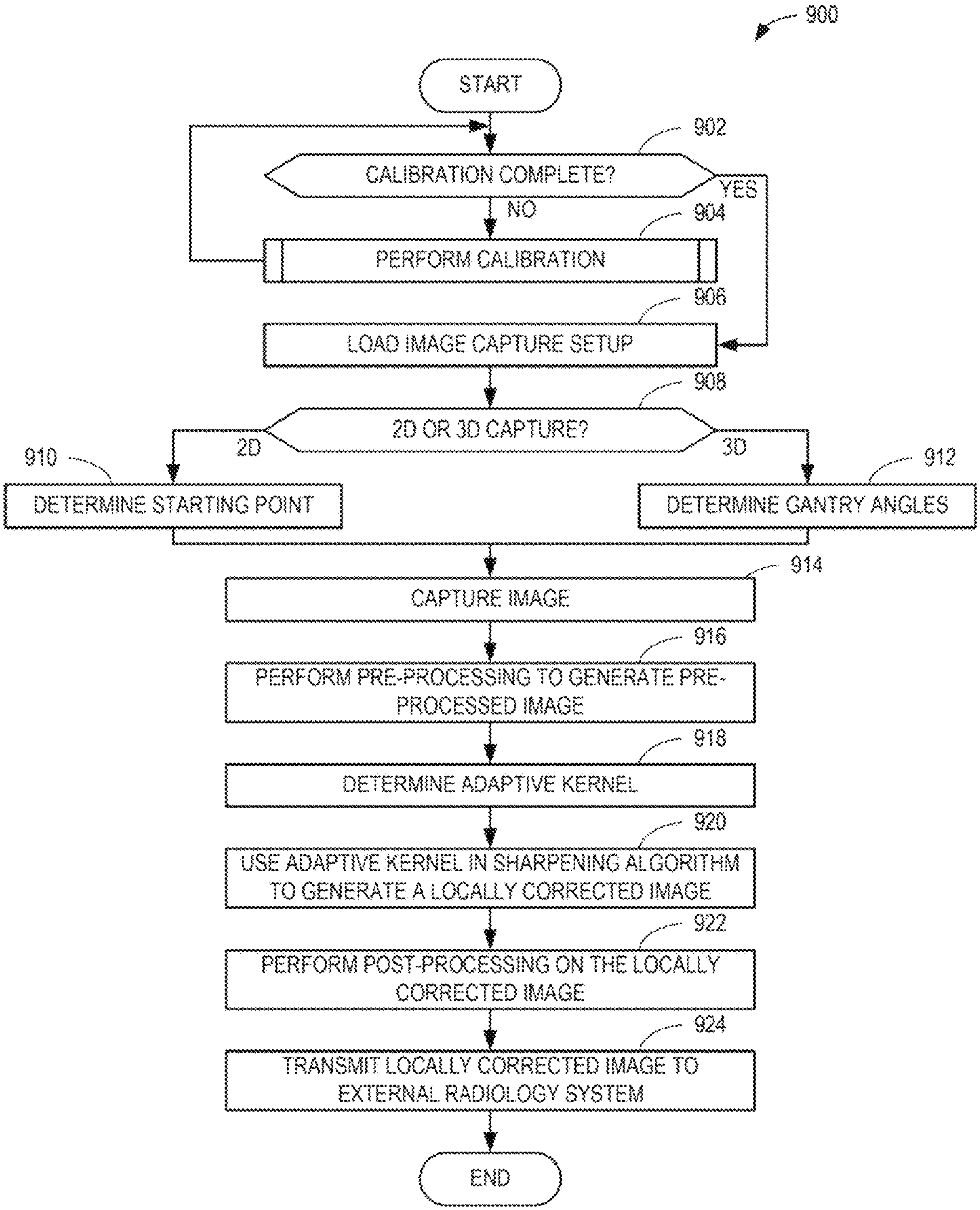
FIG. 9 is a flowchart representative of example machine readable instructions and/or example operations that may be executed, instantiated, and/or performed by example programmable circuitry to implement the medical imaging device circuitry of FIG. 7.
Figure 10:
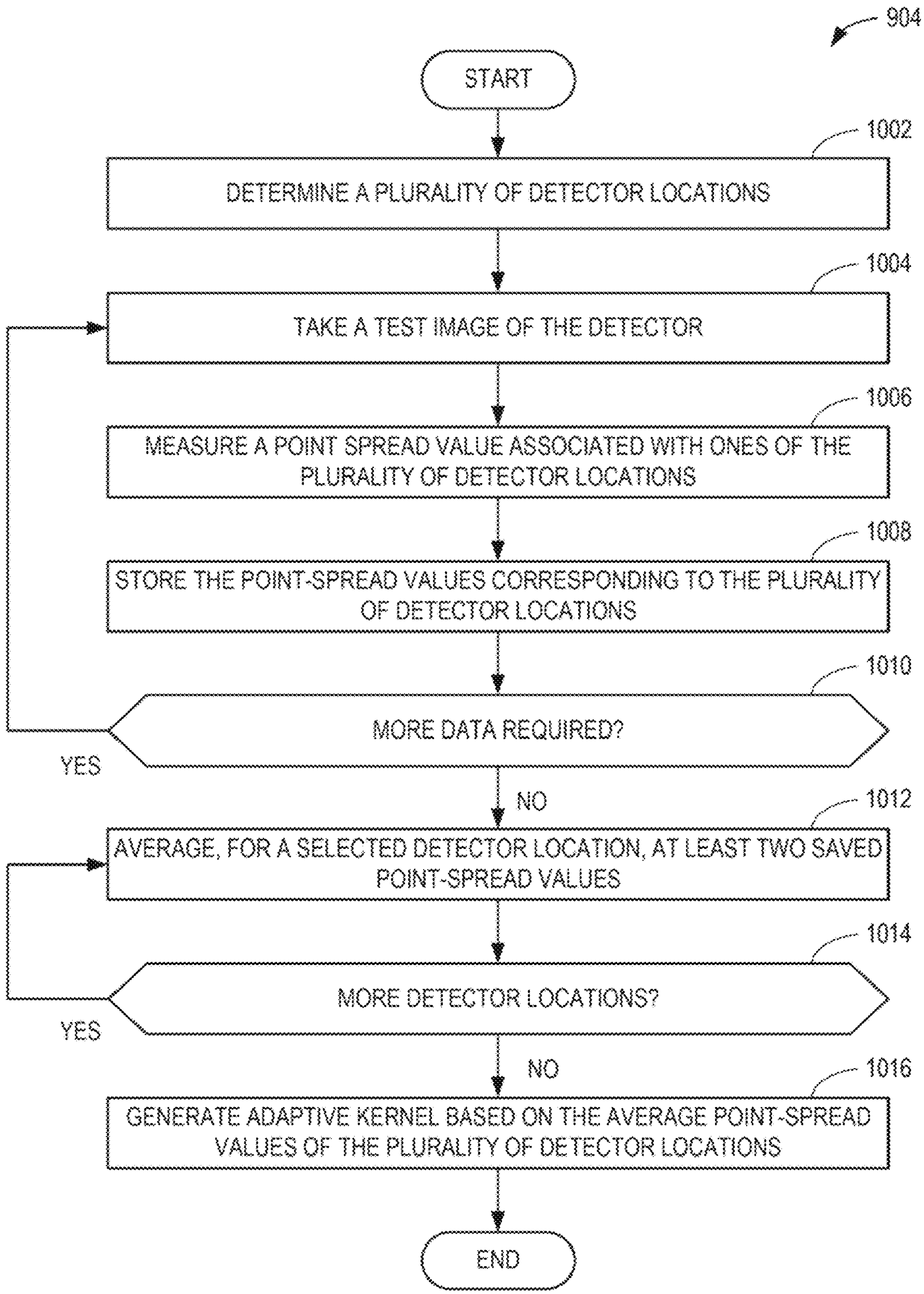
FIG. 10 is a flowchart representative of example machine readable instructions and/or example operations that may be executed, instantiated, and/or performed by example programmable circuitry to implement the kernel determiner circuitry of FIG. 8.

Flowchart(s) representative of example machine readable instructions, which may be executed by programmable circuitry to implement and/or instantiate the medical imaging device circuitry 700 of FIG. 7 and/or the kernel determiner circuitry 710 of FIG. 8 and/or representative of example operations which may be performed by programmable circuitry to implement and/or instantiate the medical imaging device circuitry 700 of FIG. 7 and/or the kernel determiner circuitry 710 of FIG. 8, are shown in FIGS. 9-10. The machine readable instructions may be one or more executable programs or portion(s) of one or more executable programs for execution by programmable circuitry such as the programmable circuitry 1312 shown in the example programmable circuitry platform 1300 discussed below in connection with FIG. 13 and/or may be one or more function (s) or portion(s) of functions to be performed by the example programmable circuitry (e.g., an FPGA) discussed below in connection with FIGS. 14 and/or 15. In some examples, the machine readable instructions cause an operation, a task, etc., to be carried out and/or performed in an automated manner in the real world. As used herein, "automated" means without human involvement.

The program may be embodied in instructions (e.g., software and/or firmware) stored on one or more non-transitory computer readable and/or machine readable storage medium such as cache memory, a magnetic-storage device or disk (e.g., a floppy disk, a Hard Disk Drive (HDD), etc.), an optical-storage device or disk (e.g., a Blu-ray disk, a Compact Disk (CD), a Digital Versatile Disk (DVD), etc.), a Redundant Array of Independent Disks (RAID), a register, ROM, a solid-state drive (SSD), SSD memory, non-volatile memory (e.g., electrically erasable programmable read-only memory (EEPROM), flash memory, etc.), volatile memory (e.g., Random Access Memory (RAM) of any type, etc.), and/or any other storage device or storage disk. The instructions of the non-transitory computer readable and/or machine readable medium may program and/or be executed by programmable circuitry located in one or more hardware devices, but the entire program and/or parts thereof could alternatively be executed and/or instantiated by one or more hardware devices other than the programmable circuitry and/or embodied in dedicated hardware. The machine readable instructions may be distributed across multiple hardware devices and/or executed by two or more hardware devices (e.g., a server and a client hardware device). For example, the client hardware device may be implemented by an endpoint client hardware device (e.g., a hardware device associated with a human and/or machine user) or an intermediate client hardware device gateway (e.g., a radio access network (RAN)) that may facilitate communication between a server and an endpoint client hardware device. Similarly, the non-transitory computer readable storage medium may include one or more mediums. Further, although the example program is described with reference to the flowchart(s) illustrated in FIGS. 9-10, many other methods of implementing the example medical imaging device circuitry 700 of FIG. 7 and/or the kernel determiner circuitry 710 of FIG. 8 may alternatively be used. For example, the order of execution of the blocks of the flowchart(s) may be changed, and/or some of the blocks described may be changed, eliminated, or combined. Additionally or alternatively, any or all of the blocks of the flow chart may be implemented by one or more hardware circuits (e.g., processor circuitry, discrete and/or integrated analog and/or digital circuitry, an FPGA, an ASIC, a comparator, an operational-amplifier (op-amp), a logic circuit, etc.) structured to perform the corresponding operation without executing software or firmware. The programmable circuitry may be distributed in different network locations and/or local to one or more hardware devices (e.g., a single-core processor (e.g., a single core CPU), a multi-core processor (e.g., a multi-core CPU, an XPU, etc.)). For example, the programmable circuitry may be a CPU and/or an FPGA located in the same package (e.g., the same integrated circuit (IC) package or in two or more separate housings), one or more processors in a single machine, multiple processors distributed across multiple servers of a server rack, multiple processors distributed across one or more server racks, etc., and/or any combination(s) thereof.

The machine readable instructions described herein may be stored in one or more of a compressed format, an encrypted format, a fragmented format, a compiled format, an executable format, a packaged format, etc. Machine readable instructions as described herein may be stored as data (e.g., computer-readable data, machine-readable data, one or more bits (e.g., one or more computer-readable bits, one or more machine-readable bits, etc.), a bitstream (e.g., a computer-readable bitstream, a machine-readable bitstream, etc.), etc.) or a data structure (e.g., as portion(s) of instructions, code, representations of code, etc.) that may be utilized to create, manufacture, and/or produce machine executable instructions. For example, the machine readable instructions may be fragmented and stored on one or more storage devices, disks and/or computing devices (e.g., servers) located at the same or different locations of a network or collection of networks (e.g., in the cloud, in edge devices, etc.). The machine readable instructions may require one or more of installation, modification, adaptation, updating, combining, supplementing, configuring, decryption, decompression, unpacking, distribution, reassignment, compilation, etc., in order to make them directly readable, interpretable, and/or executable by a computing device and/or other machine. For example, the machine readable instructions may be stored in multiple parts, which are individually compressed, encrypted, and/or stored on separate computing devices, wherein the parts when decrypted, decompressed, and/or combined form a set of computer-executable and/or machine executable instructions that implement one or more functions and/or operations that may together form a program such as that described herein.

In another example, the machine readable instructions may be stored in a state in which they may be read by programmable circuitry, but require addition of a library (e.g., a dynamic link library (DLL)), a software development kit (SDK), an application programming interface (API), etc., in order to execute the machine-readable instructions on a particular computing device or other device. In another example, the machine readable instructions may need to be configured (e.g., settings stored, data input, network addresses recorded, etc.) before the machine readable instructions and/or the corresponding program(s) can be executed in whole or in part. Thus, machine readable, computer readable and/or machine readable media, as used herein, may include instructions and/or program(s) regardless of the particular format or state of the machine readable instructions and/or program(s).

The machine readable instructions described herein can be represented by any past, present, or future instruction language, scripting language, programming language, etc. For example, the machine readable instructions may be represented using any of the following languages: C, C++, Java, C#, Perl, Python, JavaScript, HyperText Markup Language (HTML), Structured Query Language (SQL), Swift, etc.

As mentioned above, the example operations of FIGS. 9-10 may be implemented using executable instructions (e.g., computer readable and/or machine readable instructions) stored on one or more non-transitory computer readable and/or machine readable media. As used herein, the terms non-transitory computer readable medium, non-transitory computer readable storage medium, non-transitory machine readable medium, and/or non-transitory machine readable storage medium are expressly defined to include any type of computer readable storage device and/or storage disk and to exclude propagating signals and to exclude transmission media. Examples of such non-transitory computer readable medium, non-transitory computer readable storage medium, non-transitory machine readable medium, and/or non-transitory machine readable storage medium include optical storage devices, magnetic storage devices, an HDD, a flash memory, a read-only memory (ROM), a CD, a DVD, a cache, a RAM of any type, a register, and/or any other storage device or storage disk in which information is stored for any duration (e.g., for extended time periods, permanently, for brief instances, for temporarily buffering, and/or for caching of the information). As used herein, the terms "non-transitory computer readable storage device" and "non-transitory machine readable storage device" are defined to include any physical (mechanical, magnetic and/or electrical) hardware to retain information for a time period, but to exclude propagating signals and to exclude transmission media. Examples of non-transitory computer readable storage devices and/or non-transitory machine readable storage devices include random access memory of any type, read only memory of any type, solid state memory, flash memory, optical discs, magnetic disks, disk drives, and/or redundant array of independent disks (RAID) systems. As used herein, the term "device" refers to physical structure such as mechanical and/or electrical equipment, hardware, and/or circuitry that may or may not be configured by computer readable instructions, machine readable instructions, etc., and/or manufactured to execute computer-readable instructions, machine-readable instructions, etc.

FIG. 9 is a flowchart representative of example machine readable instructions and/or example operations 900 that may be executed, instantiated, and/or performed by programmable circuitry to implement the medical imaging device circuitry 700 of FIG. 7. The example machine-readable instructions and/or the example operations 900 of FIG. 9 begin at block 902, at which the kernel determiner circuitry 710 determines whether the medical imaging device 100 has been calibrated. For example, a configuration or calibration file, MTF setting, detector 108 status, etc., can be evaluated to determine whether the medical imaging device 100 has been calibrated with respect to MTF or is to be calibrated. In response to determining that calibration is complete (e.g., "YES"), control advances to block 906. Alternatively, in response to determining that calibration is not complete (e.g., "NO"), control advances to block 904. For example, the kernel determiner circuitry 710 may determine that calibration is complete if a configuration file or a calibration file is present. In some examples, the configuration file or the calibration file indicates that a set of local convolution kernels or an adaptive kernel convolution function is ready for use by the medical imaging device 100.

At block 904, the kernel determiner circuitry 710 performs calibration based on an MTF of the detector 108 to generate a set of local convolution kernels (e.g., a library of local convolution kernels) or an adaptive kernel convolution function. Further details regarding an example method that the kernel determiner circuitry 710 uses to determine the adaptive convolution kernel in the calibration process are described in connection with FIG. 10. After calibration is performed, control returns to block 902.

At block 906, the network interface 702 loads the image capture setup instructions into the image capture circuitry 704. For example, the network interface 702 may receive instructions that an image (e.g., an X-ray image, etc.) and/or a set of images is to be captured. In some examples, the dose determination circuitry 716 accesses a dose level saved in the image capture setup instructions.

At block 908, the image capture circuitry 704 determines if a two-dimensional capture or a three-dimensional capture is requested. For example, in response to determining that a two-dimensional capture is requested (e.g., "2D"), control advances to block 910. Alternatively, in response to determining that a three-dimensional capture is requested (e.g., "3D"), control advances to block 912. The example image capture circuitry 704 may determine whether to perform a two-dimensional capture or a three-dimensional capture based on instructions received by the network interface 702 (e.g., in the image capture set-up file). For example, an external system, such as a radiology workstation and/or computer-aided diagnosis software in communication with the medical imaging device 100, may determine that a single X-ray is to be taken for screening a patient. Alternatively, the external system may determine that digital breast tomosynthesis (DBT) is to be used to accurately focus on tissue of the patient.

At block 910, the image capture circuitry 704 determines a starting point. For example, the starting point is the second location 508 of FIG. 5A (e.g., detector position 5). In other examples, the starting point is the first location 504 of FIG. 5A (e.g., detector position 2). After determining the starting point, the image capture circuitry 704 moves the source 102 (FIG. 1) to be aligned over the starting point. For X-ray images, the source 102 (FIG. 1) is ready to emit an X-ray beam and captures a two-dimensional X-ray image. After block 910, control advances to block 914.

At block 912, the image capture circuitry 704 determines gantry angles. These gantry angles correspond to different positions in a revolution at which the source 102 (FIG. 1) of the medical imaging device 100 (FIG. 1) will pause to generate an image (e.g., a radiographic image). At these different gantry angles, an example beam 202 (FIG. 2) is emitted which impinges upon the detector 108 to generate an image. The medical imaging device 100 combines the plurality of images from the plurality of different gantry angles to generate a three-dimensional radiographic image. After block 912, control advances to block 914.

At block 914, the image capture circuitry 704 captures the radiographic image at the angle determined at block 912. For example, the image capture circuitry 704 may capture the radiographic image with an X-ray beam. In some examples, at block 914, the dose determination circuitry 716 confirms the radiation dose used in an X-ray image.

At block 916, the pre-processing circuitry 706 performs preprocessing on the radiographic image to generate a pre-processed image. For example, the pre-processing circuitry 706 may include using at least one of a noise filter, a gain filter, or a filter that removes bad pixels (e.g., pixels that are defective, pixels that transmit white light, pixels that do not transmit light). In some examples, pre-processing is bypassed on the radiographic image and the radiographic image is transmitted to the sharpening circuitry 708.

At block 918, the kernel determiner circuitry 710 determines an adaptive local convolution kernel (e.g., using the non-uniform convolution kernel set that includes local convolution kernels, executing the adaptive local kernel convolution function, etc.). In some examples, the kernel determiner circuitry 710 retrieves, for various detector positions and detector angles, different convolution kernel values from a previously calibrated kernel library. In other examples, the kernel determiner circuitry 710 interpolates convolution kernel values based on detector positions and detector angles that do not align with stored detector positions and stored detector angles. In yet other examples, the kernel determiner circuitry 710 is to use a continuously variable convolution kernel. The continuously variable convolution kernel is based on a position of the detector 108, for example. The kernel determiner circuitry 710 calculates, by executing the adaptive local convolution kernel function, a plurality of local convolution kernel values.

At block 920, after receiving at least one local convolution kernel from the non-uniform convolution kernel set or from the adaptive convolution kernel function, the sharpening circuitry 708 adaptively uses the at least one local convolution kernel in a sharpening algorithm to generate a locally corrected image. Rather than a standard convolution kernel (e.g., a uniform convolution kernel), the sharpening circuitry 708 uses individual ones of the local convolution kernels that correspond to particular detector locations and/or detector angles or by executing an adaptive convolution kernel function to generate a localized kernel that is dependent on detector location and/or detector angle.

In some examples, the sharpening circuitry 708 performs image convolution with the local convolution kernels to generate a corrected image (e.g., a locally corrected image matrix 424 of FIG. 4C). The sharpening circuitry 708 divides the initial image into different portions based on a number of local convolution kernels determined by the kernel determiner circuitry 710. For an example of two local convolution kernels, the example sharpening circuitry 708 then respectively, applies a first local convolution kernel to a first portion of the initial image and applies a second local convolution kernel to a second portion of the initial image. However, in other examples, more local convolution kernels can be applied in the image convolution.

At block 922, the post-processing circuitry 712 performs post processing on the corrected radiographic image. For example, the post-processing circuitry 712 performs post-processing which can further increase the contrast of small details divided by high spatial frequencies of the corrected radiographic image. Some example post-processing techniques include contrast enhancement and denoising.

At block 924, the network interface 702 transmits the locally corrected image to an external radiology system. In some examples, the network interface 702 stores the locally corrected image in the image data store 720. By transmitting the locally corrected image to the radiologist, the medical imaging device circuitry 700 improves the efficiency of using a computing device by saving processor cycles. By improving the image quality, the computing device is not required to generate a subsequent image which saves processor cycles for the computing device. After block 924, the instructions 900 end.

FIG. 10 is a flowchart representative of example machine readable instructions and/or example operations 904 that may be executed, instantiated, and/or performed by programmable circuitry to implement the kernel determiner circuitry 710 of FIG. 7 to perform calibration of the medical imaging device 100. The example machine-readable instructions and/or the example operations 904 of FIG. 9 begin at block 1002, at which the example detector location circuitry 802 determines a plurality of detector locations. For example, the example detector location circuitry 802 may determine the plurality of detector locations by loading an instruction which selects a number of detector locations to analyze. In the example of FIG. 5A, there are nine detector locations to analyze. However, in other examples, there may be more detector locations (e.g., twenty-five detector locations) or fewer detector locations (e.g., four detector locations).

At block 1004, the detector location circuitry 802 uses the example image capture circuitry 704 (FIG. 7) to take a test image of the detector 108 (FIG. 1). In some examples, the test image is taken with an X-ray source 102.

At block 1006, the example point-spread measurement circuitry 804 measures a point spread function value associated with ones of the plurality of detector locations. Some example point spread function values include a spread of 150 micrometers (e.g., 150 μm), a spread of two hundred micrometers (e.g., 200 μm), and a spread of 350 micrometers (e.g., 350 μm). However, in other examples, other point spread function values are measured using different units (e.g., centimeters, inches, micrometers, nanometers, etc.).

At block 1008, the point-spread measurement circuitry 804 stores the point spread function values corresponding to the plurality of detector locations in the example point-spread values data store 812. By storing the point-spread values associated with ones of the plurality of detector locations, the point-spread values are available for interpolation by the AI model circuitry 808.

At block 1010, the kernel calculator circuitry 810 determines if more data is required. For example, in response to determining that more data is required (e.g., "YES"), control returns to block 1004 where the example image capture circuitry 704 (FIG. 7) takes a subsequent test image of the detector 108. Alternatively, in response to determining that more data is not required (e.g., "NO"), control advances to block 1012. The example kernel calculator circuitry 810 may determine that data is required based on a precision threshold and/or a time threshold. For example, the kernel calculator circuitry 810 may determine that at least four test images are to be taken to satisfy the precision threshold. Alternatively, the kernel calculator circuitry 810 may determine that due to a patient backlog, only one test image is to be taken which satisfies a time threshold.

At block 1012, the averaging circuitry 806 averages, for a selected detector location, at least two saved point spread function values. By averaging the at least two saved point spread function values, the averaging circuitry 806 increases a precision of the point spread function value measurement. For example, if the point spread function value of a first detector location at a first time is one hundred and fifty micrometers (e.g., 150 μm) and the point spread function value of the same first detector location at a second time is 350 micrometers (e.g., 350 μm), the average of the two point spread function values is 250 micrometers (e.g., 250 μm). In the example of FIG. 5A, there are nine detector locations, and therefore the example averaging circuitry 806 determines nine average point-spread values. In some examples, such as where there is only one test image, the averaging circuitry 806 does not average the point-spread values, but merely saves the point-spread values for use by the kernel calculator circuitry 810.

At block 1014, the detector location circuitry 802 determines if there are more detector locations to analyze. For example, in response to determining that there are more detector locations to analyze (e.g., "YES"), control returns to block 1012. Alternatively, in response to determining that there are not more detector locations to analyze (e.g., "NO"), control advances to block 1016. The example detector location circuitry 802 may determine there are more detector locations based on if some detector locations have an average point-spread value and some detector locations have multiple individual point-spread values, but not an average point-spread value.

At block 1016, the example kernel calculator circuitry 810 generates the adaptive convolution kernel based on the average point spread function values of the plurality of center locations. In some examples, the adaptive convolution kernel is selected from a pre-generated set or library of non-uniform local convolution kernels. The example kernel calculator circuitry 810 may generate a non-uniform kernel set of local convolution kernels by using an inverse Fourier transform on the average point spread function values, for example. The example kernel calculator circuitry 810 stores a correspondence for the local convolution kernels ($K_{x,y}$) based on center locations. For example, the kernel calculator circuitry 810 stores that a first local convolution kernel ($K_{1,1}$) was generated based on a first detector location that is in a first spot in a horizontal direction and a first spot in a vertical direction. The first local convolution kernel ($K_{1,1}$) is transmitted for use by the sharpening circuitry 708 (FIG. 7) at block 918 of FIG. 9. In some examples, the kernel calculator circuitry 810 accesses pre-determined local convolution kernels from a library of convolution kernels rather than determining the local convolution kernels based on test images. In such examples, the kernel calculator circuitry 810 uses the AI model circuitry 808 to interpolate local convolution kernels if the determined center locations (e.g., impact locations) of the scintillated particles of the initial image 312 do not match (e.g., correspond) to saved local convolution kernels. In other examples, the adaptive convolution kernel is generated using an adaptive local convolution kernel function which is based on different parameters (e.g., angle, position, dose, etc.). After block 1016, the instructions 916 end and/or return to block 918 of FIG. 9.

FIG. 11 is an example graph 1100 illustrating modulation transfer responses 1106, 1108, 1110 for multiple detector positions using a single uniform kernel and a locally corrected modulation transfer response 1104 with respect to an "ideal" or perfect modulator transfer response 1102. As shown in the example of FIG. 11, an ideal MTF remains at 1.0. However, as discussed above, the detector 108 does not respond in an ideal manner. Using a traditional, single convolution kernel uniform MTF compensation produces different MTF responses 1106, 1108, 1110 for different positions or areas of the detector 108. Using an adaptive convolution kernel (e.g., set of local convolution kernels or adaptive convolution local kernel algorithm, etc.) enables different areas of the detector 108 to be locally compensated such that a consistent MTF response 1104 is achieved. Further, as shown in the example of FIG. 11, the MTF response 1104 resulting from adaptive, localized convolution kernel adjustment better approaches the "ideal" detector response 1102.

FIG. 12 is a MTF graph that includes the frequency represented as line pairs per millimeter across the X-axis and the MTF ratio along the Y-axis. The ideal MTF is a constant value of 1.0 shown as a solid line 1202, while the real MTF as measured from the medical imaging device 100 (FIG. 1) is shown as thick dashed line 1206. Based on different doses, the sharpened MTF is shown as thin dotted lines 1204. As illustrated in the MTF graph 1200, as the dose increases, the level of compensation increases to increase the MTF values for more line pairs per millimeter.

Figure 13:
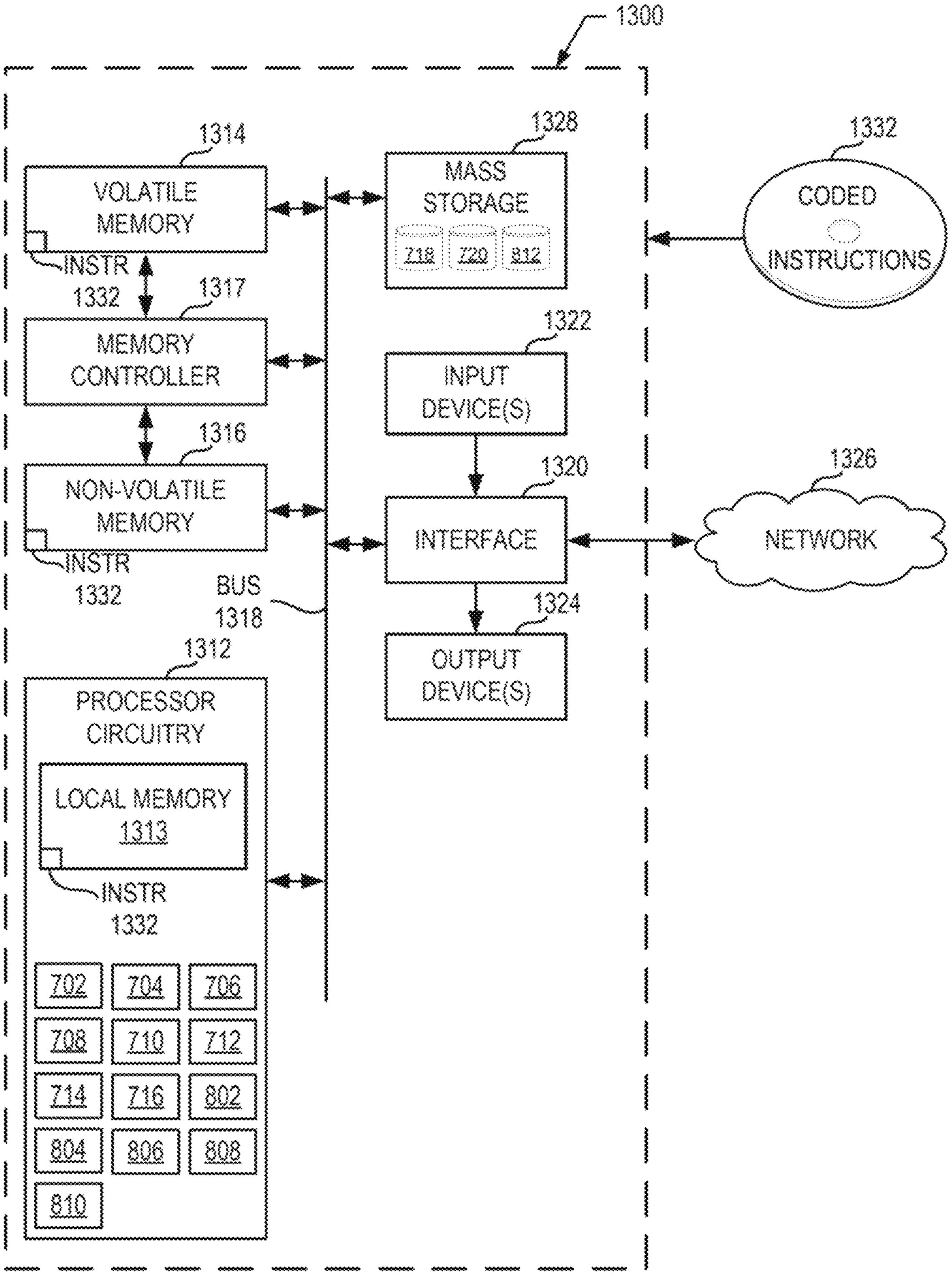
FIG. 13 is a block diagram of an example processing platform including programmable circuitry structured to execute, instantiate, and/or perform the example machine readable instructions and/or perform the example operations of FIGS. 9-10 to implement the medical imaging device circuitry of FIG. 7 and/or the kernel determiner circuitry of FIG. 8.

FIG. 13 is a block diagram of an example programmable circuitry platform 1300 structured to execute and/or instantiate the example machine-readable instructions and/or the example operations of FIGS. 9-10 to implement the medical imaging device circuitry 700 of FIG. 7 and/or the kernel determiner circuitry 710 of FIG. 8. The programmable circuitry platform 1300 can be, for example, a server, a personal computer, a workstation, a self-learning machine (e.g., a neural network), or any other type of computing and/or electronic device.

The programmable circuitry platform 1300 of the illustrated example includes programmable circuitry 1312. The programmable circuitry 1312 of the illustrated example is hardware. For example, the programmable circuitry 1312 can be implemented by one or more integrated circuits, logic circuits, FPGAs, microprocessors, CPUs, GPUs, DSPs, and/or microcontrollers from any desired family or manufacturer. The programmable circuitry 1312 may be implemented by one or more semiconductor based (e.g., silicon based) devices.

In this example, the programmable circuitry 1312 implements an example network interface 702, example image capture circuitry 704, example pre-processing circuitry 706, example sharpening circuitry 708, example kernel determiner circuitry 710, example post-processing circuitry 712, example modulation transfer function circuitry 714, example dose determination circuitry 716, example detector location circuitry 802, example point-spread measurement circuitry 804, example averaging circuitry 806, example AI model circuitry 808, and example kernel calculator circuitry 810.

The programmable circuitry 1312 of the illustrated example includes a local memory 1313 (e.g., a cache, registers, etc.). The programmable circuitry 1312 of the illustrated example is in communication with main memory 1314, 1316, which includes a volatile memory 1314 and a non-volatile memory 1316, by a bus 1318. The volatile memory 1314 may be implemented by Synchronous Dynamic Random Access Memory (SDRAM), Dynamic Random Access Memory (DRAM), RAMBUS® Dynamic Random Access Memory (RDRAM®), and/or any other type of RAM device. The non-volatile memory 1316 may be implemented by flash memory and/or any other desired type of memory device. Access to the main memory 1314, 1316 of the illustrated example is controlled by a memory controller 1317. In some examples, the memory controller 1317 may be implemented by one or more integrated circuits, logic circuits, microcontrollers from any desired family or manufacturer, or any other type of circuitry to manage the flow of data going to and from the main memory 1314, 1316.

The programmable circuitry platform 1300 of the illustrated example also includes interface circuitry 1320. The interface circuitry 1320 may be implemented by hardware in accordance with any type of interface standard, such as an Ethernet interface, a universal serial bus (USB) interface, a Bluetooth® interface, a near field communication (NFC) interface, a Peripheral Component Interconnect (PCI) interface, and/or a Peripheral Component Interconnect Express (PCIe) interface.

In the illustrated example, one or more input devices 1322 are connected to the interface circuitry 1320. The input device(s) 1322 permit(s) a user (e.g., a human user, a machine user, etc.) to enter data and/or commands into the programmable circuitry 1312. The input device(s) 1322 can be implemented by, for example, an audio sensor, a microphone, a camera (still or video), a keyboard, a button, a mouse, a touchscreen, a trackpad, a trackball, an isopoint device, and/or a voice recognition system.

One or more output devices 1324 are also connected to the interface circuitry 1320 of the illustrated example. The output device(s) 1324 can be implemented, for example, by display devices (e.g., a light emitting diode (LED), an organic light emitting diode (OLED), a liquid crystal display (LCD), a cathode ray tube (CRT) display, an in-place switching (IPS) display, a touchscreen, etc.), a tactile output device, a printer, and/or speaker. The interface circuitry 1320 of the illustrated example, thus, typically includes a graphics driver card, a graphics driver chip, and/or graphics processor circuitry such as a GPU.

The interface circuitry 1320 of the illustrated example also includes a communication device such as a transmitter, a receiver, a transceiver, a modem, a residential gateway, a wireless access point, and/or a network interface to facilitate exchange of data with external machines (e.g., computing devices of any kind) by a network 1326. The communication can be by, for example, an Ethernet connection, a digital subscriber line (DSL) connection, a telephone line connection, a coaxial cable system, a satellite system, a beyond-line-of-sight wireless system, a line-of-sight wireless system, a cellular telephone system, an optical connection, etc.

The programmable circuitry platform 1300 of the illustrated example also includes one or more mass storage discs or devices 1328 to store firmware, software, and/or data. Examples of such mass storage discs or devices 1328 include magnetic storage devices (e.g., floppy disk, drives, HDDs, etc.), optical storage devices (e.g., Blu-ray disks, CDs, DVDs, etc.), RAID systems, and/or solid-state storage discs or devices such as flash memory devices and/or SSDs.

The machine readable instructions 1332, which may be implemented by the machine readable instructions of FIGS. 9-10, may be stored in the mass storage device 1328, in the volatile memory 1314, in the non-volatile memory 1316, and/or on at least one non-transitory computer readable storage medium such as a CD or DVD which may be removable.

Figure 14:
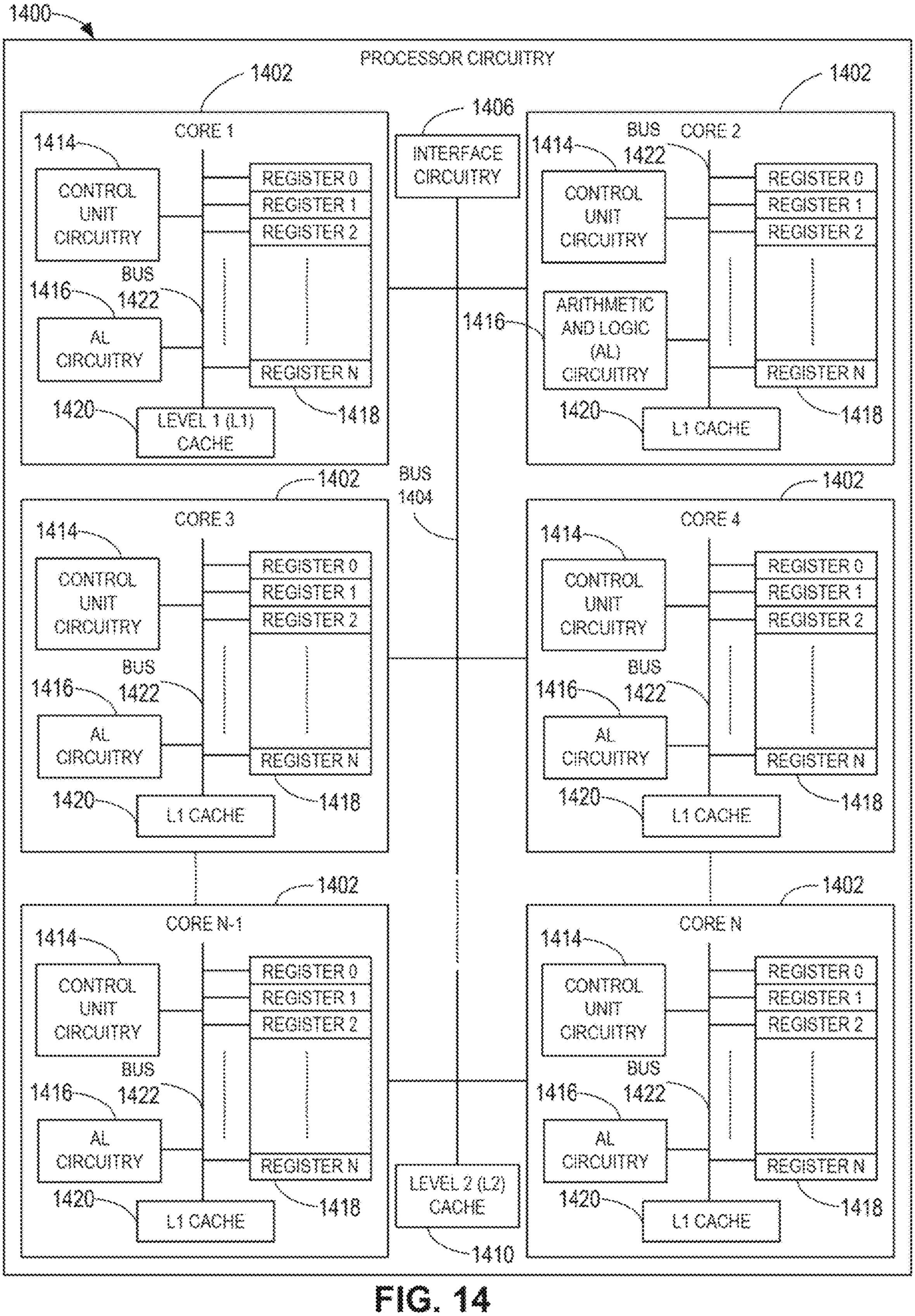
FIG. 14 is a block diagram of an example implementation of the programmable circuitry of FIG. 13.

FIG. 14 is a block diagram of an example implementation of the programmable circuitry 1312 of FIG. 13. In this example, the programmable circuitry 1312 of FIG. 13 is implemented by a microprocessor 1400. For example, the microprocessor 1400 may be a general-purpose microprocessor (e.g., general-purpose microprocessor circuitry). The microprocessor 1400 executes some or all of the machine-readable instructions of the flowcharts of FIGS. 9-10 to effectively instantiate the circuitry of FIG. 2 as logic circuits to perform operations corresponding to those machine readable instructions. In some such examples, the circuitry of FIG. 8 is instantiated by the hardware circuits of the microprocessor 1400 in combination with the machine-readable instructions. For example, the microprocessor 1400 may be implemented by multi-core hardware circuitry such as a CPU, a DSP, a GPU, an XPU, etc. Although it may include any number of example cores 1402 (e.g., 1 core), the microprocessor 1400 of this example is a multi-core semiconductor device including N cores. The cores 1402 of the microprocessor 1400 may operate independently or may cooperate to execute machine readable instructions. For example, machine code corresponding to a firmware program, an embedded software program, or a software program may be executed by one of the cores 1402 or may be executed by multiple ones of the cores 1402 at the same or different times. In some examples, the machine code corresponding to the firmware program, the embedded software program, or the software program is split into threads and executed in parallel by two or more of the cores 1402. The software program may correspond to a portion or all of the machine readable instructions and/or operations represented by the flowcharts of FIGS. 9-10.

The cores 1402 may communicate by a first example bus 1404. In some examples, the first bus 1404 may be implemented by a communication bus to effectuate communication associated with one(s) of the cores 1402. For example, the first bus 1404 may be implemented by at least one of an Inter-Integrated Circuit (I2C) bus, a Serial Peripheral Interface (SPI) bus, a PCI bus, or a PCIe bus. Additionally or alternatively, the first bus 1404 may be implemented by any other type of computing or electrical bus. The cores 1402 may obtain data, instructions, and/or signals from one or more external devices by example interface circuitry 1406. The cores 1402 may output data, instructions, and/or signals to the one or more external devices by the interface circuitry 1406. Although the cores 1402 of this example include example local memory 1420 (e.g., Level 1 (L1) cache that may be split into an L1 data cache and an L1 instruction cache), the microprocessor 1400 also includes example shared memory 1410 that may be shared by the cores (e.g., Level 2 (L2 cache)) for high-speed access to data and/or instructions. Data and/or instructions may be transferred (e.g., shared) by writing to and/or reading from the shared memory 1410. The local memory 1420 of each of the cores 1402 and the shared memory 1410 may be part of a hierarchy of storage devices including multiple levels of cache memory and the main memory (e.g., the main memory 1314, 1316 of FIG. 13). Typically, higher levels of memory in the hierarchy exhibit lower access time and have smaller storage capacity than lower levels of memory. Changes in the various levels of the cache hierarchy are managed (e.g., coordinated) by a cache coherency policy.

Each core 1402 may be referred to as a CPU, DSP, GPU, etc., or any other type of hardware circuitry. Each core 1402 includes control unit circuitry 1414, arithmetic and logic (AL) circuitry (sometimes referred to as an ALU) 1416, a plurality of registers 1418, the local memory 1420, and a second example bus 1422. Other structures may be present. For example, each core 1402 may include vector unit circuitry, single instruction multiple data (SIMD) unit circuitry, load/store unit (LSU) circuitry, branch/jump unit circuitry, floating-point unit (FPU) circuitry, etc. The control unit circuitry 1414 includes semiconductor-based circuits structured to control (e.g., coordinate) data movement within the corresponding core 1402. The AL circuitry 1416 includes semiconductor-based circuits structured to perform one or more mathematic and/or logic operations on the data within the corresponding core 1402. The AL circuitry 1416 of some examples performs integer based operations. In other examples, the AL circuitry 1416 also performs floating-point operations. In yet other examples, the AL circuitry 1416 may include first AL circuitry that performs integer-based operations and second AL circuitry that performs floating-point operations. In some examples, the AL circuitry 1416 may be referred to as an Arithmetic Logic Unit (ALU).

The registers 1418 are semiconductor-based structures to store data and/or instructions such as results of one or more of the operations performed by the AL circuitry 1416 of the corresponding core 1402. For example, the registers 1418 may include vector register(s), SIMD register(s), general-purpose register(s), flag register(s), segment register(s), machine-specific register(s), instruction pointer register(s), control register(s), debug register(s), memory management register(s), machine check register(s), etc. The registers 1418 may be arranged in a bank as shown in FIG. 14. Alternatively, the registers 1418 may be organized in any other arrangement, format, or structure, such as by being distributed throughout the core 1402 to shorten access time. The second bus 1422 may be implemented by at least one of an I2C bus, a SPI bus, a PCI bus, or a PCIe bus.

Each core 1402 and/or, more generally, the microprocessor 1400 may include additional and/or alternate structures to those shown and described above. For example, one or more clock circuits, one or more power supplies, one or more power gates, one or more cache home agents (CHAs), one or more converged/common mesh stops (CMSs), one or more shifters (e.g., barrel shifter(s)) and/or other circuitry may be present. The microprocessor 1400 is a semiconductor device fabricated to include many transistors interconnected to implement the structures described above in one or more integrated circuits (ICs) contained in one or more packages.

The microprocessor 1400 may include and/or cooperate with one or more accelerators (e.g., acceleration circuitry, hardware accelerators, etc.). In some examples, accelerators are implemented by logic circuitry to perform certain tasks more quickly and/or efficiently than can be done by a general-purpose processor. Examples of accelerators include ASICs and FPGAs such as those discussed herein. A GPU, DSP and/or other programmable device can also be an accelerator. Accelerators may be on-board the microprocessor 1400, in the same chip package as the microprocessor 1400 and/or in one or more separate packages from the microprocessor 1400.

Figure 15:
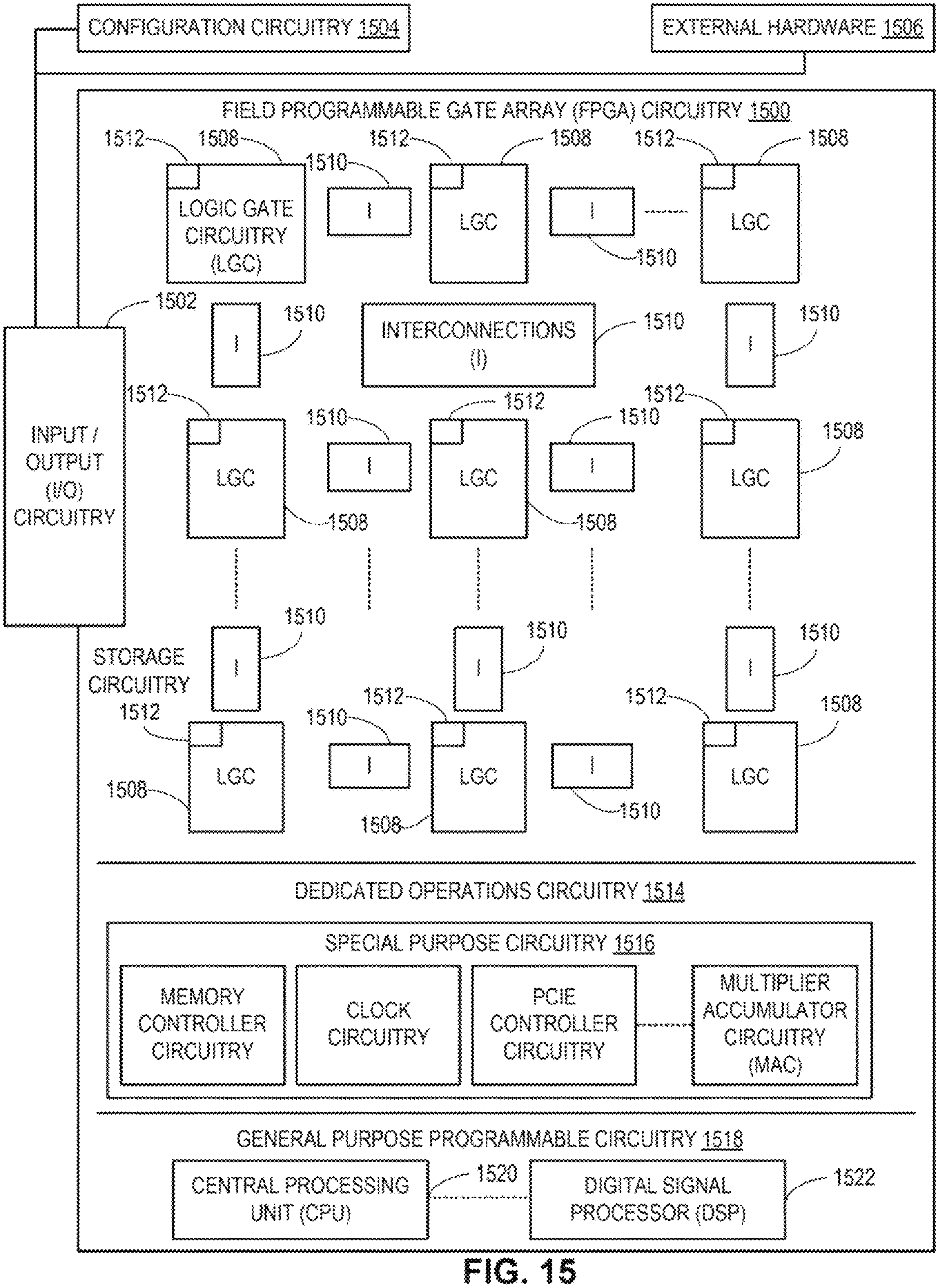
FIG. 15 is a block diagram of another example implementation of the programmable circuitry of FIG. 13.

FIG. 15 is a block diagram of another example implementation of the programmable circuitry 1312 of FIG. 13. In this example, the programmable circuitry 1312 is implemented by FPGA circuitry 1500. For example, the FPGA circuitry 1500 may be implemented by an FPGA. The FPGA circuitry 1500 can be used, for example, to perform operations that could otherwise be performed by the example microprocessor 1400 of FIG. 14 executing corresponding machine readable instructions. However, once configured, the FPGA circuitry 1500 instantiates the operations and/or functions corresponding to the machine readable instructions in hardware and, thus, can often execute the operations/functions faster than they could be performed by a general-purpose microprocessor executing the corresponding software.

More specifically, in contrast to the microprocessor 1400 of FIG. 14 described above (which is a general purpose device that may be programmed to execute some or all of the machine readable instructions represented by the flowchart (s) of FIGS. 9-10 but whose interconnections and logic circuitry are fixed once fabricated), the FPGA circuitry 1500 of the example of FIG. 15 includes interconnections and logic circuitry that may be configured, structured, programmed, and/or interconnected in different ways after fabrication to instantiate, for example, some or all of the operations/functions corresponding to the machine readable instructions represented by the flowchart(s) of FIGS. 9-10. In particular, the FPGA circuitry 1500 may be thought of as an array of logic gates, interconnections, and switches. The switches can be programmed to change how the logic gates are interconnected by the interconnections, effectively forming one or more dedicated logic circuits (unless and until the FPGA circuitry 1500 is reprogrammed). The configured logic circuits enable the logic gates to cooperate in different ways to perform different operations on data received by input circuitry. Those operations may correspond to some or all of the instructions (e.g., the software and/or firmware) represented by the flowchart(s) of FIGS. 9-10. As such, the FPGA circuitry 1500 may be configured and/or structured to effectively instantiate some or all of the operations/functions corresponding to the machine readable instructions of the flowchart(s) of FIGS. 9-10 as dedicated logic circuits to perform the operations/functions corresponding to those software instructions in a dedicated manner analogous to an ASIC. Therefore, the FPGA circuitry 1500 may perform the operations/functions corresponding to the some or all of the machine readable instructions of FIGS. 9-10 faster than the general-purpose microprocessor can execute the same.

In the example of FIG. 15, the FPGA circuitry 1500 is configured and/or structured in response to being programmed (and/or reprogrammed one or more times) based on a binary file. In some examples, the binary file may be compiled and/or generated based on instructions in a hardware description language (HDL) such as Lucid, Very High Speed Integrated Circuits (VHSIC) Hardware Description Language (VHDL), or Verilog. For example, a user (e.g., a human user, a machine user, etc.) may write code or a program corresponding to one or more operations/functions in an HDL; the code/program may be translated into a low-level language as needed; and the code/program (e.g., the code/program in the low-level language) may be converted (e.g., by a compiler, a software application, etc.) into the binary file. In some examples, the FPGA circuitry 1500 of FIG. 15 may access and/or load the binary file to cause the FPGA circuitry 1500 of FIG. 15 to be configured and/or structured to perform the one or more operations/functions. For example, the binary file may be implemented by a bit stream (e.g., one or more computer-readable bits, one or more machine-readable bits, etc.), data (e.g., computer-readable data, machine-readable data, etc.), and/or machine-readable instructions accessible to the FPGA circuitry 1500 of FIG. 15 to cause configuration and/or structuring of the FPGA circuitry 1500 of FIG. 15, or portion(s) thereof.

In some examples, the binary file is compiled, generated, transformed, and/or otherwise output from a uniform software platform utilized to program FPGAs. For example, the uniform software platform may translate first instructions (e.g., code or a program) that correspond to one or more operations/functions in a high-level language (e.g., C, C++, Python, etc.) into second instructions that correspond to the one or more operations/functions in an HDL. In some such examples, the binary file is compiled, generated, and/or otherwise output from the uniform software platform based on the second instructions. In some examples, the FPGA circuitry 1500 of FIG. 15 may access and/or load the binary file to cause the FPGA circuitry 1500 of FIG. 15 to be configured and/or structured to perform the one or more operations/functions. For example, the binary file may be implemented by a bit stream (e.g., one or more computer-readable bits, one or more machine-readable bits, etc.), data (e.g., computer-readable data, machine-readable data, etc.), and/or machine-readable instructions accessible to the FPGA circuitry 1500 of FIG. 15 to cause configuration and/or structuring of the FPGA circuitry 1500 of FIG. 15, or portion(s) thereof.

The FPGA circuitry 1500 of FIG. 15, includes example input/output (I/O) circuitry 1502 to obtain and/or output data to/from example configuration circuitry 1504 and/or external hardware 1506. For example, the configuration circuitry 1504 may be implemented by interface circuitry that may obtain a binary file, which may be implemented by a bit stream, data, and/or machine-readable instructions, to configure the FPGA circuitry 1500, or portion(s) thereof. In some such examples, the configuration circuitry 1504 may obtain the binary file from a user, a machine (e.g., hardware circuitry (e.g., programmable or dedicated circuitry) that may implement an Artificial Intelligence/Machine Learning (AI/ML) model to generate the binary file), etc., and/or any combination(s) thereof). In some examples, the external hardware 1506 may be implemented by external hardware circuitry. For example, the external hardware 1506 may be implemented by the microprocessor 1400 of FIG. 14.

The FPGA circuitry 1500 also includes an array of example logic gate circuitry 1508, a plurality of example configurable interconnections 1510, and example storage circuitry 1512. The logic gate circuitry 1508 and the configurable interconnections 1510 are configurable to instantiate one or more operations/functions that may correspond to at least some of the machine readable instructions of FIGS. 9-10 and/or other desired operations. The logic gate circuitry 1508 shown in FIG. 15 is fabricated in blocks or groups. Each block includes semiconductor-based electrical structures that may be configured into logic circuits. In some examples, the electrical structures include logic gates (e.g., And gates, Or gates, Nor gates, etc.) that provide basic building blocks for logic circuits. Electrically controllable switches (e.g., transistors) are present within each of the logic gate circuitry 1508 to enable configuration of the electrical structures and/or the logic gates to form circuits to perform desired operations/functions. The logic gate circuitry 1508 may include other electrical structures such as look-up tables (LUTs), registers (e.g., flip-flops or latches), multiplexers, etc.

The configurable interconnections 1510 of the illustrated example are conductive pathways, traces, vias, or the like that may include electrically controllable switches (e.g., transistors) whose state can be changed by programming (e.g., using an HDL instruction language) to activate or deactivate one or more connections between one or more of the logic gate circuitry 1508 to program desired logic circuits.

The storage circuitry 1512 of the illustrated example is structured to store result(s) of the one or more of the operations performed by corresponding logic gates. The storage circuitry 1512 may be implemented by registers or the like. In the illustrated example, the storage circuitry 1512 is distributed amongst the logic gate circuitry 1508 to facilitate access and increase execution speed.

The example FPGA circuitry 1500 of FIG. 15 also includes example dedicated operations circuitry 1514. In this example, the dedicated operations circuitry 1514 includes special purpose circuitry 1516 that may be invoked to implement commonly used functions to avoid the need to program those functions in the field. Examples of such special purpose circuitry 1516 include memory (e.g., DRAM) controller circuitry, PCIe controller circuitry, clock circuitry, transceiver circuitry, memory, and multiplier-accumulator circuitry. Other types of special purpose circuitry may be present. In some examples, the FPGA circuitry 1500 may also include example general purpose programmable circuitry 1518 such as an example CPU 1520 and/or an example DSP 1522. Other general purpose programmable circuitry 1518 may additionally or alternatively be present such as a GPU, an XPU, etc., that can be programmed to perform other operations.

Although FIGS. 14 and 15 illustrate two example implementations of the programmable circuitry 1312 of FIG. 13, many other approaches are contemplated. For example, FPGA circuitry may include an on-board CPU, such as one or more of the example CPU 1520 of FIG. 14. Therefore, the programmable circuitry 1312 of FIG. 13 may additionally be implemented by combining at least the example microprocessor 1400 of FIG. 14 and the example FPGA circuitry 1500 of FIG. 15. In some such hybrid examples, one or more cores 1402 of FIG. 14 may execute a first portion of the machine readable instructions represented by the flowchart(s) of FIGS. 9-10 to perform first operation(s)/function(s), the FPGA circuitry 1500 of FIG. 15 may be configured and/or structured to perform second operation(s)/function(s) corresponding to a second portion of the machine readable instructions represented by the flowcharts of FIG. 9-10, and/or an ASIC may be configured and/or structured to perform third operation(s)/function(s) corresponding to a third portion of the machine readable instructions represented by the flowcharts of FIGS. 9-10.

It should be understood that some or all of the circuitry of FIG. 8 may, thus, be instantiated at the same or different times. For example, same and/or different portion(s) of the microprocessor 1400 of FIG. 14 may be programmed to execute portion(s) of machine-readable instructions at the same and/or different times. In some examples, same and/or different portion(s) of the FPGA circuitry 1500 of FIG. 15 may be configured and/or structured to perform operations/functions corresponding to portion(s) of machine-readable instructions at the same and/or different times.

In some examples, some or all of the circuitry of FIG. 8 may be instantiated, for example, in one or more threads executing concurrently and/or in series. For example, the microprocessor 1400 of FIG. 14 may execute machine readable instructions in one or more threads executing concurrently and/or in series. In some examples, the FPGA circuitry 1500 of FIG. 15 may be configured and/or structured to carry out operations/functions concurrently and/or in series. Moreover, in some examples, some or all of the circuitry of FIG. 8 may be implemented within one or more virtual machines and/or containers executing on the microprocessor 1400 of FIG. 14.

In some examples, the programmable circuitry 1312 of FIG. 13 may be in one or more packages. For example, the microprocessor 1400 of FIG. 14 and/or the FPGA circuitry 1500 of FIG. 15 may be in one or more packages. In some examples, an XPU may be implemented by the programmable circuitry 1312 of FIG. 13, which may be in one or more packages. For example, the XPU may include a CPU (e.g., the microprocessor 1400 of FIG. 14, the CPU 1520 of FIG. 15, etc.) in one package, a DSP (e.g., the DSP 1522 of FIG. 15) in another package, a GPU in yet another package, and an FPGA (e.g., the FPGA circuitry 1500 of FIG. 15) in still yet another package.

Figure 16:
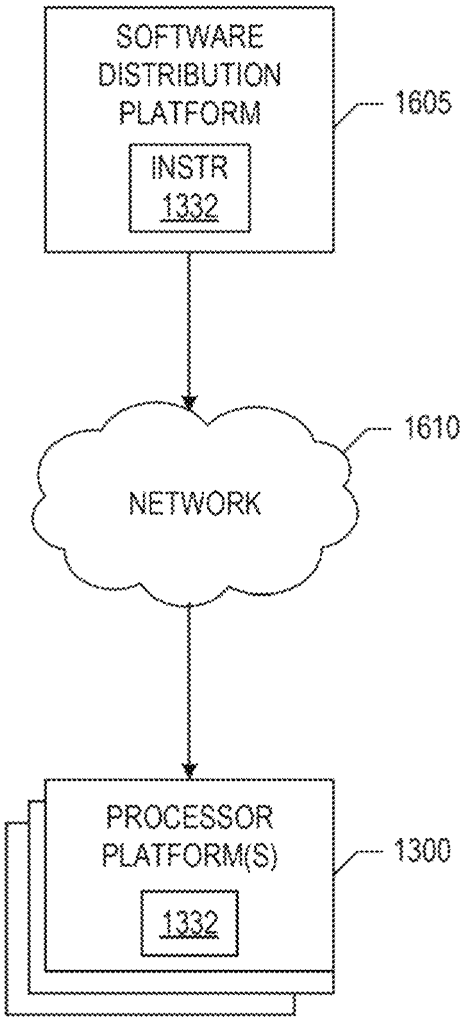
FIG. 16 is a block diagram of an example software/firmware/instructions distribution platform (e.g., one or more servers) to distribute software, instructions, and/or firmware (e.g., corresponding to the example machine readable instructions of FIGS. 9-10) to client devices associated with end users and/or consumers (e.g., for license, sale, and/or use), retailers (e.g., for sale, re-sale, license, and/or sub-license), and/or original equipment manufacturers (OEMs) (e.g., for inclusion in products to be distributed to, for example, retailers and/or to other end users such as direct buy customers).

A block diagram illustrating an example software distribution platform 1605 to distribute software such as the example machine readable instructions 1332 of FIG. 13 to other hardware devices (e.g., hardware devices owned and/or operated by third parties from the owner and/or operator of the software distribution platform) is illustrated in FIG. 16. The example software distribution platform 1605 may be implemented by any computer server, data facility, cloud service, etc., capable of storing and transmitting software to other computing devices. The third parties may be customers of the entity owning and/or operating the software distribution platform 1605. For example, the entity that owns and/or operates the software distribution platform 1605 may be a developer, a seller, and/or a licensor of software such as the example machine readable instructions 1332 of FIG. 13. The third parties may be consumers, users, retailers, OEMs, etc., who purchase and/or license the software for use and/or re-sale and/or sub-licensing. In the illustrated example, the software distribution platform 1605 includes one or more servers and one or more storage devices. The storage devices store the machine readable instructions 1332, which may correspond to the example machine readable instructions of FIGS. 9-10, as described above. The one or more servers of the example software distribution platform 1605 are in communication with an example network 1610, which may correspond to any one or more of the Internet and/or any of the example networks described above. In some examples, the one or more servers are responsive to requests to transmit the software to a requesting party as part of a commercial transaction. Payment for the delivery, sale, and/or license of the software may be handled by the one or more servers of the software distribution platform and/or by a third party payment entity. The servers enable purchasers and/or licensors to download the machine readable instructions 1332 from the software distribution platform 1605. For example, the software, which may correspond to the example machine readable instructions of FIG. 9-10, may be downloaded to the example programmable circuitry platform 1300, which is to execute the machine readable instructions 1332 to implement the medical imaging device circuitry 700. In some examples, one or more servers of the software distribution platform 1605 periodically offer, transmit, and/or force updates to the software (e.g., the example machine readable instructions 1332 of FIG. 13) to ensure improvements, patches, updates, etc., are distributed and applied to the software at the end user devices. Although referred to as software above, the distributed "software" could alternatively be firmware.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc., may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, or (7) A with B and with C. As used herein in the context of describing structures, components, items, objects and/or things, the phrase "at least one of A and B" is intended to refer to implementations including any of (1) at least one A, (2) at least one B, or (3) at least one A and at least one B. Similarly, as used herein in the context of describing structures, components, items, objects and/or things, the phrase "at least one of A or B" is intended to refer to implementations including any of (1) at least one A, (2) at least one B, or (3) at least one A and at least one B. As used herein in the context of describing the performance or execution of processes, instructions, actions, activities, etc., the phrase "at least one of A and B" is intended to refer to implementations including any of (1) at least one A, (2) at least one B, or (3) at least one A and at least one B. Similarly, as used herein in the context of describing the performance or execution of processes, instructions, actions, activities, etc., the phrase "at least one of A or B" is intended to refer to implementations including any of (1) at least one A, (2) at least one B, or (3) at least one A and at least one B.

As used herein, singular references (e.g., "a", "an", "first", "second", etc.) do not exclude a plurality. The term "a" or "an" object, as used herein, refers to one or more of that object. The terms "a" (or "an"), "one or more", and "at least one" are used interchangeably herein. Furthermore, although individually listed, a plurality of means, elements, or actions may be implemented by, e.g., the same entity or object. Additionally, although individual features may be included in different examples or claims, these may possibly be combined, and the inclusion in different examples or claims does not imply that a combination of features is not feasible and/or advantageous.

As used herein, unless otherwise stated, the term "above" describes the relationship of two parts relative to Earth. A first part is above a second part, if the second part has at least one part between Earth and the first part. Likewise, as used herein, a first part is "below" a second part when the first part is closer to the Earth than the second part. As noted above, a first part can be above or below a second part with one or more of: other parts therebetween, without other parts therebetween, with the first and second parts touching, or without the first and second parts being in direct contact with one another.

As used in this patent, stating that any part (e.g., a layer, film, area, region, or plate) is in any way on (e.g., positioned on, located on, disposed on, or formed on, etc.) another part, indicates that the referenced part is either in contact with the other part, or that the referenced part is above the other part with one or more intermediate part(s) located therebetween.

As used herein, connection references (e.g., attached, coupled, connected, and joined) may include intermediate members between the elements referenced by the connection reference and/or relative movement between those elements unless otherwise indicated. As such, connection references do not necessarily infer that two elements are directly connected and/or in fixed relation to each other. As used herein, stating that any part is in "contact" with another part is defined to mean that there is no intermediate part between the two parts.

Unless specifically stated otherwise, descriptors such as "first," "second," "third," etc., are used herein without imputing or otherwise indicating any meaning of priority, physical order, arrangement in a list, and/or ordering in any way, but are merely used as labels and/or arbitrary names to distinguish elements for ease of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for identifying those elements distinctly within the context of the discussion (e.g., within a claim) in which the elements might, for example, otherwise share a same name.

As used herein, "approximately" and "about" modify their subjects/values to recognize the potential presence of variations that occur in real world applications. For example, "approximately" and "about" may modify dimensions that may not be exact due to manufacturing tolerances and/or other real world imperfections as will be understood by persons of ordinary skill in the art. For example, "approximately" and "about" may indicate such dimensions may be within a tolerance range of +/−10% unless otherwise specified herein.

As used herein "substantially real time" refers to occurrence in a near instantaneous manner recognizing there may be real world delays for computing time, transmission, etc. Thus, unless otherwise specified, "substantially real time" refers to real time+1 second.

As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

As used herein, "programmable circuitry" is defined to include (i) one or more special purpose electrical circuits (e.g., an application specific circuit (ASIC)) structured to perform specific operation(s) and including one or more semiconductor-based logic devices (e.g., electrical hardware implemented by one or more transistors), and/or (ii) one or more general purpose semiconductor-based electrical circuits programmable with instructions to perform specific functions(s) and/or operation(s) and including one or more semiconductor-based logic devices (e.g., electrical hardware implemented by one or more transistors). Examples of programmable circuitry include programmable microprocessors such as Central Processor Units (CPUs) that may execute first instructions to perform one or more operations and/or functions, Field Programmable Gate Arrays (FPGAs) that may be programmed with second instructions to cause configuration and/or structuring of the FPGAs to instantiate one or more operations and/or functions corresponding to the first instructions, Graphics Processor Units (GPUs) that may execute first instructions to perform one or more operations and/or functions, Digital Signal Processors (DSPs) that may execute first instructions to perform one or more operations and/or functions, XPUs, Network Processing Units (NPUs) one or more microcontrollers that may execute first instructions to perform one or more operations and/or functions and/or integrated circuits such as Application Specific Integrated Circuits (ASICs). For example, an XPU may be implemented by a heterogeneous computing system including multiple types of programmable circuitry (e.g., one or more FPGAs, one or more CPUs, one or more GPUs, one or more NPUs, one or more DSPs, etc., and/or any combination(s) thereof), and orchestration technology (e.g., application programming interface(s) (API(s)) that may assign computing task(s) to whichever one(s) of the multiple types of programmable circuitry is/are suited and available to perform the computing task(s).

As used herein integrated circuit/circuitry is defined as one or more semiconductor packages containing one or more circuit elements such as transistors, capacitors, inductors, resistors, current paths, diodes, etc. For example an integrated circuit may be implemented as one or more of an ASIC, an FPGA, a chip, a microchip, programmable circuitry, a semiconductor substrate coupling multiple circuit elements, a system on chip (SoC), etc.

From the foregoing, it will be appreciated that example systems, apparatus, articles of manufacture, and methods have been disclosed that sharpen a radiographic image with a non-uniform kernel. Disclosed systems, apparatus, articles of manufacture, and methods improve the efficiency of using a computing device by saving processor cycles. By improving the image quality, the computing device is not required to generate a subsequent image which saves processor cycles for the computing device. Additionally, localized generation and application of kernels, rather than a single uniform kernel applied to an entire detector image, provides a cleaner, clearer, and more accurate image for automated processing and analysis to drive other systems in patient diagnosis and treatment. Disclosed systems, apparatus, articles of manufacture, and methods are accordingly directed to one or more improvement(s) in the operation of a machine such as a computer or other electronic and/or mechanical device.

Example methods, apparatus, systems, and articles of manufacture to sharpen a radiographic image with an adaptive kernel by increasing a uniformity in sharpness are disclosed herein. Further examples and combinations thereof include the following:

Example 1 includes an apparatus to sharpen a radiographic image comprising interface circuitry, machine readable instructions, and programmable circuitry to at least one of instantiate or execute the machine readable instructions to capture a radiographic image with a detector receiving a beam from a source, and perform a digital correction to the radiographic image to generate a digital image with increased uniformity in sharpness compared to the radiographic image.

Example 2 includes the apparatus of example 1, wherein the digital correction is local spatial filtering.

Example 3 includes any of example 1 and example 2, wherein the digital correction is performed by using an adaptive convolution kernel.

Example 4 includes any of examples 1-3, wherein the adaptive convolution kernel is generated using an adaptive convolution kernel function that generates non-stationary convolution kernels.

Example 5 includes any of examples 1-4, wherein the adaptive convolution kernel function generates coefficient values based on a coordinate location on a surface of the detector.

Example 6 includes any of examples 1-5, wherein the adaptive convolution kernel function generates coefficient values based on an angle between the source and a coordinate location on a surface of the detector.

Example 7 includes any of examples 1-6, wherein the adaptive convolution kernel function generates coefficient values based on a current tomographic angle of a tomographic imaging tube relative to a normal of a plane of the detector.

Example 8 includes any of examples 1-7, wherein the adaptive convolution kernel function generates coefficient values based on dose.

Example 9 includes any of examples 1-8, wherein the adaptive convolution kernel is generated by selection from a set of local convolution kernels determined based on at least one of a position on an area of the detector, an angle between the source and a coordinate location on a surface of the detector, and dose.

Example 10 includes any of examples 1-9, wherein a first local convolution kernel is used for sharpening a first portion of the radiographic image that corresponds to a first region on a surface of the detector and a second local convolution kernel is used for sharpening a second portion of the radiographic image that corresponds to a second region on the surface of the detector, the first region different from the second region.

Example 11 includes any of examples 1-10, further including storing the digital image and transmitting the digital image to an external system.

Example 12 includes any of examples 1-11, wherein the radiographic image is a two-dimensional X-ray image.

Example 13 includes any of examples 1-12, wherein the radiographic image is a three-dimensional tomosynthesis image, wherein the three-dimensional tomosynthesis image is obtained by computation from a set of two-dimensional X-ray images captured at different angles corresponding to a first revolution of the apparatus.

Example 14 includes any of examples 1-13, further including measuring a point spread function value at a specific location on the detector of the apparatus, the point spread function value used in calibrating a set of local convolution kernels.

Example 15 includes any of examples 1-14, further including averaging a first point spread function value at a first location on the detector and a second point spread function value at the first location on the detector to generate an average point spread function value, the average point spread function value used in calibrating the set of local convolution kernels.

Example 16 includes a non-transitory machine readable storage medium comprising instructions to cause programmable circuitry to at least capture a first radiographic image with a medical imaging device, and perform a localized digital correction to the first radiographic image to generate a digital image with increased uniformity in sharpness compared to the radiographic image, the localized digital correction performed by at least one of linear convolution kernel using a non-stationary convolution kernel function that depends on position of the medical imaging device or a set of local convolution kernels, with ones of the local convolution kernels determined based on a position on a detector surface of the medical imaging device.

Example 17 includes example 16, wherein the instructions are to cause the programmable circuitry to increase modulation transfer function values associated with the first radiographic image.

Example 18 includes a method for sharpening a radiographic image comprising capturing a radiographic image with a detector receiving a beam from a source, performing a digital correction to generate a locally corrected radiographic image, and transmitting the locally corrected radiographic image to an external system.

Example 19 includes example 18, further including calibrating an imaging machine by performing a measurement process that quantifies a level of non-uniformity in blurring of radiographic images captured by the imaging machine, the calibrating to occur before capturing the radiographic image.

Example 20 includes any of example 18 and example 19, further including calibrating an imaging machine by determining a first local convolution kernel of a library of local convolution kernels by determining a plurality of detector locations, taking a test image of the detector, measuring a plurality of point-spread values associated with ones of the plurality of detector locations, and storing the plurality of point-spread values corresponding to the plurality of detector locations.

The following claims are hereby incorporated into this Detailed Description by this reference. Although certain example systems, apparatus, articles of manufacture, and methods have been disclosed herein, the scope of coverage of this patent is not limited thereto. On the contrary, this patent covers all systems, apparatus, articles of manufacture, and methods fairly falling within the scope of the claims of this patent.

What is claimed is:

1. An apparatus to sharpen a radiographic image comprising:

interface circuitry;

machine readable instructions; and programmable circuitry to at least one of instantiate or execute the machine readable instructions to:

capture a radiographic image with a detector receiving a beam from a source; and perform a localized digital correction to the radiographic image to generate a digital image with increased uniformity in sharpness compared to the radiographic image, wherein the radiographic image is a three-dimensional tomosynthesis image, and wherein the three-dimensional tomosynthesis image is obtained by computation from a set of two-dimensional X-ray images captured at different angles corresponding to a first revolution of the apparatus.

2. The apparatus of claim 1, wherein the localized digital correction includes local spatial filtering of the radiographic image.

3. The apparatus of claim 1, wherein the localized digital correction is performed by applying an adaptive convolution kernel to the radiographic image.

4. The apparatus of claim 3, wherein the adaptive convolution kernel is generated using an adaptive convolution kernel function that generates non-stationary convolution kernels to be applied to areas of the radiographic image.

5. The apparatus of claim 4, wherein the adaptive convolution kernel function generates coefficient values for the non-stationary convolution kernels to be applied to the radiographic image based on a coordinate location on a surface of the detector.

6. The apparatus of claim 4, wherein the adaptive convolution kernel function generates coefficient values for the non-stationary convolution kernels to be applied to the radiographic image based on an angle between the source and a coordinate location on a surface of the detector.

7. The apparatus of claim 4, wherein the adaptive convolution kernel function generates coefficient values based on a current tomographic angle of a tomographic imaging tube relative to a normal of a plane of the detector.

8. The apparatus of claim 4, wherein the adaptive convolution kernel function generates coefficient values for the non-stationary convolution kernels to be applied to the radiographic image based on dose.

9. The apparatus of claim 3, wherein the adaptive convolution kernel is generated by selection from a set of local convolution kernels determined based on at least one of a position on an area of the detector, an angle between the source and a coordinate location on a surface of the detector, or dose.

10. The apparatus of claim 9, wherein a first local convolution kernel is used for sharpening a first portion of the radiographic image that corresponds to a first region on a surface of the detector and a second local convolution kernel is used for sharpening a second portion of the radiographic image that corresponds to a second region on the surface of the detector, the first region different from the second region.

11. The apparatus of claim 1, wherein the programmable circuitry is to store the digital image and transmit the digital image to an external system.

12. The apparatus of claim 1, wherein the radiographic image is a two-dimensional X-ray image.

13. The apparatus of claim 1, wherein the programable circuitry is to measure a point spread function value at a specific location on the detector of the apparatus, the point spread function value used in calibrating a set of local convolution kernels.

14. The apparatus of claim 13, wherein the programmable circuitry is to average a first point spread function value at a first location on the detector and a second point spread function value at the first location on the detector to generate an average point spread function value, the average point spread function value used in calibrating the set of local convolution kernels.

15. A non-transitory machine readable storage medium comprising instructions to cause programmable circuitry to at least:

capture a first radiographic image with a detector of a medical imaging device; and perform a localized digital correction to the first radiographic image to generate a digital image with increased uniformity in sharpness compared to the radiographic image, the localized digital correction performed by at least one of linear convolution kernel using a non-stationary convolution kernel function that depends on position of the medical imaging device or a set of local convolution kernels, with ones of the local convolution kernels determined based on a position on a detector surface of the medical imaging device, wherein the instructions are to cause the programmable circuitry to calibrate the medical imaging device according to a modulation transfer function of the detector.

16. A method for sharpening a radiographic image comprising:

calibrating an imaging device by measuring to quantify a level of non-uniformity in blurring of radiographic images captured by the imaging device, the calibrating to occur before capturing the radiographic image;

capturing a radiographic image with a detector receiving a beam from a source;

performing a localized digital correction to generate a locally corrected radiographic image; and transmitting the locally corrected radiographic image to an external system.

17. The method of claim 16, further including calibrating an imaging device by determining a first local convolution kernel of a library of local convolution kernels by:

determining a plurality of detector locations;

taking a test image of the detector;

measuring a plurality of point-spread values associated with ones of the plurality of detector locations; and storing the plurality of point-spread values corresponding to the plurality of detector locations.

* * * * *